United States Patent [19]
Daynes et al.

[11] Patent Number: 5,837,269
[45] Date of Patent: Nov. 17, 1998

[54] VACCINE COMPOSITIONS AND METHOD FOR ENHANCING AN IMMUNE RESPONSE

[75] Inventors: Raymond A. Daynes, Park City; Barbara A. Araneo, Salt Lake City, both of Utah

[73] Assignee: University of Utah Research Foundation, Salt Lake City, Utah

[21] Appl. No.: 487,173

[22] Filed: Jun. 7, 1995

Related U.S. Application Data

[63] Continuation-in-part of Ser. No. 123,843, Sep. 9, 1993, Pat. No. 5,562,910, which is a continuation-in-part of Ser. No. 13,972, Feb. 4, 1993, abandoned, and Ser. No. 779,499, Oct. 18, 1991, abandoned, which is a continuation-in-part of Ser. No. 412,270, Sep. 25, 1989, abandoned.

[51] Int. Cl.$^6$ .......................... A61K 39/00; A61K 31/56; A61K 31/59

[52] U.S. Cl. .................. 424/278.1; 424/93.1; 424/184.1; 424/212.1; 424/209.1; 424/219.1; 424/217.1; 424/225.1; 424/245.1; 424/247.1; 424/231.1; 424/234.1; 424/256.1; 424/85.2; 514/171; 514/178; 514/175; 514/885; 552/621

[58] Field of Search ................................ 424/93.1, 184.1, 424/212.1, 209.1, 219.1, 217.1, 225.1, 245.1, 247.1, 231.1, 278.1, 254.1, 256.1, 85.2; 514/171, 178, 725, 885; 552/621

[56] References Cited

U.S. PATENT DOCUMENTS

| | | |
|---|---|---|
| 4,698,221 | 10/1987 | Straub . |
| 5,077,284 | 12/1991 | Loria et al. . |
| 5,098,899 | 3/1992 | Gilbert et al. . |
| 5,206,008 | 4/1993 | Loria . |
| 5,407,684 | 4/1995 | Loria et al. . |

FOREIGN PATENT DOCUMENTS

| | | |
|---|---|---|
| 2 204 237 | 11/1988 | United Kingdom . |
| WO 91/04030 | 4/1991 | WIPO . |

OTHER PUBLICATIONS

Abe, J. et al. (1989). "A Synthetic Analogue of Vitamin $D_3$, 22–Oxa–1α25–Dihydroxyvitamin $D_3$, is a Potent Modulator of In vivo Immunoregulating Activity Without Inducing Hypercalcemia in Mice," *Endocrinol.* 124:2645–2647.

Abraham, E. et al. (1992). "Intranasal Immunization with Liposomes Containing IL–2 Enhances Bacterial Polysaccharide Antigen–Specific Pulmonary Secretory Antibody Response," *J. Immunol.* 149: 3719–3726.

Araneo, B.A. et al. (1991). "Dihydrotestosterone Exerts a Depressive Influence on the Production of Interleukin–4 (IL–4), IL–5, and γ–Interferon, But Not IL–2 by Activated Murine T Cells," *Blood* 78:688–699.

Araneo, B.A. et al. (1993). "Administration of Dehydroepiandrosterone to Burned Mice Preserves Normal Immunologic Competence," *Arch. Surg.* 128:318–325.

Araneo, B.A. et al. (1993). "Reversal of the Immunosenescent Phenotype by Dehydroepiandrosterone: Hormone Treatment Provides an Adjuvant Effect on the Immunization of Aged Mice with Recombinant Hepatitis B Surface Antigen," *J. Infect. Dis.* 167:830–840.

AyanlarBatuman, O. et al. (1991). "Regulation of Transforming Growth Factor–β1 Gene Expression by Glucocorticoids in Normal Human T Lymphocytes," *J. Clin. Invest.* 88:1574–1580.

Bhalla, A.K. (1989). "Hormones and the Immune Response," *Ann. of Rheumatic Dis.* 48:1–6.

Bienenstock, J. et al. (1983). "Regulation of Lumphoblast Traffic and Localization in Mucosal Tissues, with Emphasis on IgA," *Federation Proceedings* 42:3213–3217.

Bikle, D.D. (1992). "Clinical counterpoint: Vitamin D: New Actions, New Analogs, New Therapeutic Potential," *Endocrine Reviews* 13:765–784.

Binderup, L. et al. (1992). "Commentary: Immunological Properties of Vitamin D Analogues and Metabolites," *Biochem. Pharmacol.* 43:1885–1892.

Casson, P.R. et al. (1993). "Oral Dehydroepiandrosterone in Physiologic Doses Modulates Immune Function in Postmenopausal Women," *Am. J. Obstet. Gynecol.* 169:1536–1539.

Coffman, R.L. (1989). "T–Helper Heterogeneity and Immune Response Patterns," *Hosp. Practice (Aug. 15, 1989)*:101–133.

Coffman, R.L. et al. (1989). "Transforming Growth Factor β Specifically Enhances IgA Production by Lipopolysaccharide–Stimulated Murine B Lymphocytes," *J. Exp. Med.* 170:1039–1044.

(List continued on next page.)

*Primary Examiner*—Anthony C. Caputa
*Assistant Examiner*—Khalid Masood
*Attorney, Agent, or Firm*—Rothwell, Figg, Ernst & Kurz, P.C.

[57] ABSTRACT

The invention relates to a vaccine which comprises an antigen and an immune response augmenting agent. The immune response augmenting agent is capable of enhancing T cell lymphokine production. Suitable immune response augmenting agents include, but are not limited to, DHEA, DHEA-derivatives and DHEA congeners.

The invention also relates to a method for enhancing a vaccine-induced humoral immune response which comprises administering a vaccine which comprises an antigen and an immunomodulator. The immunomodulator may be an immune response augmenting agent, a lymphoid organ modifying agent or a mixture of the immune response augmenting agent and lymphoid organ modifying agent. Suitable lymphoid organ modifying agents include, but are not limited to, 1,25-dihydroxy Vitamin $D_3$, 25-hydroxy Vitamin $D_3$, biologically active 1,25-dihydroxy Vitamin $D_3$, derivatives which are capable of activating the intra-cellular Vitamin $D_3$ receptor, all trans-retinoic acid, retinoic acid derivatives, retinol, retinol derivatives and glucocorticoid. Alternatively, the method for enhancing a vaccine-induced humoral immune response comprises separately administering the immunomodulator and a vaccine containing an antigen.

50 Claims, 18 Drawing Sheets

OTHER PUBLICATIONS

Dawson, M.I. et al. (1981). "Aromatic Retinoic Acid Analogues. Synthesis and Pharmacological Activity," *J. Med. Chem.* 24:583–592.

Dawson, M.I. et al. (1981). "Retinoci Acid Analogues with Ring Modifications. Synthesis and Pharmacological Activity," *J. Med. Chem.* 24:1214–1223.

Daynes, R.A. et al. (1989). "Contrasting Effects of Glucocorticoids on the Capacity of T. Cells to Produce the Growth Factors Interleukin 2 and Interleukin 4," *Eur. J. Immunol.* 19:2319–2325.

Daynes, R.A. et al. (1990). "Regulation of Murine Lymphokine Production In Vivo: II. Dehydroepiandrosterone is a Natual Enhancer of Interleukin 2 Synthesis by Helper T Cells," *Eur. J. Immunol.* 20:793–802.

Daynes, R.A. et al. (1990). "Regulation of Murine Lymphokine Production In Vivo: III. The Lymphoid Tissue Microenvironment Exerts Regulatory Influences Over T Helper Cell Function," *J. Exp. Med.* 171:979–996.

Daynes, R.A. et al. (1991). "Locally active steroid hormones may facilitate compartmentalization of immunity by regulating the types of lymphokines produce by helper T cells," *Research in Immunology* 142:40–45.

Daynes, R.A. and Araneo, B.A. (1992). "Prevention and Reversal of some Age–Associated Changes in Immunologic Responses by Supplemental Dehydroepiandrosterone Sulphate Therapy," *Aging: Immunology and Infectious Disease* 3:135–154.

Daynes, R.A. et al. (1992). "Natural Regulators of T–Cell Lymphokine Production In Vivo," *J. Immunother.* 12:174–179.

Defrance, T. et al. (1992). "Interleukin 10 and Transforming Growth Factor β Co–Operate to Induce Anti–CD40–Activated Naive Human B Cells to Secrete Immunoglobulin A," *J. Exp. Med.* 175:671–682.

Dinarello, C.A. et al. (1987). "Current Concepts: Lymphokines," *New Eng. J. Med.* 317:940–945.

Ernst, P.B. et al. (1987). "Immunity in Mucosal Tissues," in *Basic & Clinical Immunology*, Sixth Ed. (eds. Stites, D.P. et al.),(Appleton & Lange, Norwalk, CT), pp. 159–166.

Finkelman, F.D. et al. (1990). "Lymphokine Control of In Vivo Immunoglobulin Isotype Selection," *Ann. Rev. Immunol.* 8:303–333.

Finkelman, R.D. et al. (1991). "Vitamin D deficiency causes a selective reduction in deposition of transforming growth factor β in rat bone: Possible mechanism for impaired osteoinduction," *Proc. Natl. Acad. Sci. USA* 88:3657–3660.

Garg, M. et al. (1993). "Reversal of Age–Associated Decline in Immune Response to Pnu–Immune Vaccine by Supplementation with the Steroid Hormone Dehydroepiandrosterone," *Infect. Immun.* 61:2238–2241.

Glick, A.B. et al. (1989). "Retinoic acid induces tranforming growth factr–β2 in cultured keratinocytes and mouse epidermis," *Cell Regulation* 1:87–97.

Granner, D.K. (1988). "Hormones of the Adrenal Cotex," *Harper's Biochemistry*, pp. 511–523.

Hahn–Zoric, M. et al. (1989). "The Influence on the Secretory IgA Antibody Levels in Lactating Women of Oral Typhoid and Parenteral Cholera Vaccines Given Alone or in Combination," *Scand. J. Infect. Dis.* 21:421–426.

Hewison, M. (1992). "Vitamin D and the Immune System," *J. Endocrinol.* 132:173–175.

Holmgren, J. (1991), "Mucosal immunity and vaccination," *FEMS Microbiology Immunology* 89:1–10.

Kawanishi, H. et al. (1983). "Mechanisms Regulating IgA Class–Specific Immunoglobulin Production in Murine Gut–Associated Lumphoid Tissues," *J. Exp. Med.* 157:433–450.

Kiyono, H. et al. (1984). "Isotype Specificity of Helper T Cell Clones," *J. Exp. Med.* 159:798–811.

Komori, T. et al. (1985). "The Effect of 1α–Hydroxyvitamin $D_3$ on Primary Antibody Formation in Mice," *Immunopharmacol.* 9:141–146.

Lebman, D.A. et al. (1990). "Molecular Characterization of Germ–Line immunoglobulin A Transcripts Produced During Transforming Growth Factor β–Induced Isotype Switching," *Proc. Natl. Acad. Sci. USA* 87: 3962–3966.

Lebman, D.A. et al. (1990). "Mechanism for Transforming Growth Factor β and IL–2 Enhancement of IgA Expression in Lipopolysaccharide–Stimulated B Cell Cultures," *J. Immunology* 144:952–959.

Lemire, J.M. (1992), "Immunomodulatory Role of 1,25–Dihydroxyvitamin $D_3$," *J. Cell. Biochem.* 49:26–31.

Liew, F.Y. et al. (1984). "Cross–protection in mice infected with influenza A virus by the respiratory route is correlated with local IgA antibody rather than serum antibody or cytotoxic T cell reactivity," *Eur. J. Immunol.* 14:350–356.

Loria, R.M. and Padgett, D.A. (1992). "Mobilizatin of Cutaneous Immunity for Systemic Protection Against Infections," *Ann, N.Y. Acad. Sci.* 650:363–366.

Mbawuike, I.N. et al. (1990). "Enhancement of the Protective Efficacy of Inactivated Influenza A Virus Vaccine in Aged Mie by IL–2 Liposomes," *Vaccine* 8:347–352.

McBride, B.W. et al. (1988). "Mucosal antibody response to vaginal infection with herpes simplex virus in pre–vaccinated guinea–pigs," *Vaccine* 6:414–418.

Meikle, A.W. et al. (1991). "Adrenal Androgen Secretion and Biologic Effects," *Endocin. Metab. Clin. N. Am.* 20:381–400.

Mestecky, J. (1987). "The Common Mucosal System and Current Strategies for Induction of Immune Responses in External Secretions," *J. Clin. Immunol.* 7:265–276.

Müller, K. et al. (1992). "Inhibition of Human T Lynphocyte Proliferation and Cytokine Production by 1,25–dihydroxyvitamin D3, Differential Effects on CD45RA+ and CD45RO+ Cells," *Autoimmunity* 14:37–43.

Murray, R.K. et al. (eds.) (1988). *Harper's Biochemistry* (21st Edition), pp. 507–508 (Appleton & Lange, Norwalk, CT).

Nossal, G.J.V. (1987). "Current Concepts: Immunology: The Basic Components of the Immune System," *New Eng. J. Med.* 316:1320–1325.

Nunberg, J.H. et al. (1989). "Interleukin 2 Acts as an Adjuvant to Increase the Potency of Inactivated Rabies Virus Vaccine," *Proc. Natl. Acad. Sci. USA* 86:4240–4243.

Petkovich, P.M. et al. (1987). "1,25–Dihydroxyvitamin D3 Increases Epidermal Growth Factor Receptors and Transforming Growth Factor β–Like Activity in a Bone–Derived Cell Line," *J. Biol. Chem.* 262:13424–13428.

Pfeilschifter, J. et al. (1987). "Modulation of Type β Transforming Growth Factor Activity in Bone Cultures by Osteotropic Hormones," *Proc. Natl. Acad. Sci. USA* 84:2024–2048.

Quiding, M. et al. (1991). "Intestinal Immune Responses in Humans," *J. Clin. Invest.* 88:143–148.

Rasmussen, K.R. et al. (1992). "Dehydroepiandrosterone–Induced Reduction of Cryptosporidium Parvum Infections in Aged Syrain Golden Hamsters,," *J. Parasitol.* 78:554–557.

Rigby, W.F.C. (1988). "The Immunobiology of Vitamin D," *Immunol. Today* 9:54–57.

Risdon, G. et al. (1990). "Mechanisms of Chemoprevention by Dietary Dehydroisoandrosterone: Inhibition of Lymphopoiesis," *Am. J. Pathol.* 136:759–769.

Roberts, A.B. et al. (1992). "Mechanistic Interrelationships Between Two Superfamilies: The Steroid/Retinoid Receptors and Transforming Growth Factor–$\beta$," *Cancer Surveys* 14:205–220.

Roitt, I.M. (1988). *Essential Immunology,* Blackwell Scientific Publications, p. 172.

Shull, M.M. et a. (1992). "Targeted Disruption of the Mouse Transforming Growth Factor–$\beta$–1 Gene Results in Multifocal Inflammatory Disease," *Nature* 359:693–699.

Suzuki, T. et al. (1991). "Dehydroepiandrosterone Enhances IL2 Production and Cytotoxic Function of Human T Cells," *Clin. Immunol. Immunopathol.* 61:202–211.

Tabata, T. et al. (1986). "The Effect of 1$\alpha$–Hydroxyvitamin $D_3$ on Cell–Mediated Immunity in Hemodialyzed Patients," *J. Clin. Endocrin. Metab.* 63:1218–1221.

van den Wall Bake, A.W.L. et al. (1992). "Transforming Growth Factor–$\beta$ Inhibits the Production of IgG, IgM, and IgA in Human Lymphocyte Cultures," *Cellular Immunology* 144:417–428.

van Vlasselaer, P. et al. (1992). "Transforming Growth Factor–$\beta$ Directs IgA Switching in Human B Cells," *J. Immunol.* 148:2062–2067.

Weinberg, A. et al. (1988). "Recombinant Interleukin 2 as an Adjuvant for Vaccine–Induced Protection," *J. Immunol.* 140:294–299.

Weindruch, R. et al. (1984). "Food Intake Reduction and Immunologic Alterations in Mice Fed Dehydroepiandrosterone," *Exp. Gerontol.* 19:297–304.

Weksler, M.E. (1993). "Immune senescence and adrenal steroids: immune dysregultion and the action of dehydroepiandrosterine (DHEA) in old animals," *Eur. J. Clin Pharmacol.* 45[*Suppl. 1*]:S21–S23.

Wiedmeier, S.E. et al. (1991). "Thymic Modulation of IL–2 and IL–4 Synthesis by Peripheral T Cells," *Cell. Immunol.* 135:501–518.

Windholtz, M. et al. (eds.) (1976). *The Merck Index,* pp. 1289–1291 (Merck & Co., Inc., Rahway, N.J.).

Wu, C.Y. et al. (1991). "Glucocorticoids Suppress the Production of Interleukin 4 by Human Lymphocytes," *Eur. J. Immunol.* 21:2645–2647.

VACCINE COMPOSITIONS AND METHOD FOR ENHANCING AN IMMUNE RESPONSE

CROSS-REFERENCE TO RELATED APPLICATIONS

This Application is a continuation-in-part of application U.S. Ser. No. 08/123,843, (U.S. Pat. No. 5,562,810) filed Sep. 9, 1993, which is a continuation-in-part of application U.S. Ser. No. 08/013,972, filed Feb. 4, 1993 now abandoned and of application U.S. Ser. No. 07/779,499, filed Oct. 18, 1991 now abandoned. Ser. No. 07/779,499 now abandoned is a continuation-in-part of application U.S. Ser. No. 07/412,270, filed Sep. 25, 1989 now abandoned. The specification of each of these applications is incorporated by reference herein in its entirety.

TECHNICAL FIELD

The invention relates to vaccine compositions and methods of vaccination which provide for higher antibody titres in the vaccinated individuals. More specifically, the invention relates to vaccine compositions containing immune response augmenting agents, such as dehydroepiandrosterone (DHEA), DHEA congeners and DHEA derivatives as immunomodulators in the vaccine compositions. The invention further relates to methods for enhancing an antigen specific circulating antibody immune response.

BACKGROUND OF THE INVENTION

The publications and other materials used herein to illuminate the background of the invention, or provide additional details respecting its practice, are incorporated by reference.

It is known that lymphocytes exported from the thymus undergo a series of differentiation events which confer upon them the capacity to recognize and respond to specific peptide antigens presented appropriately in the context of self major histocompatibility complex (MHC) molecules. Mechanistically, thymic maturation is a complex process which includes an irreversible rearrangement of T cell receptor genes, the cell surface expression of these gene products as disulfide-linked heterodimers, positive and negative selection processes to provide appropriate restriction and avoidance of self-reactivity, and the synthesis and expression of CD4 or CD8 as accessory adhesion molecules. Microenvironmental influences within the thymus play an essential role in the fidelity of this process.

Subsequent to leaving the thymic microenvironment, mature T lymphocytes gain access to the recirculating T cell pool where they move freely via the blood between mucosal and nonmucosal lymphoid compartments in the mammalian host (Hamann et al. (1989). *Immunol. Rev.* 108: 19). T-lymphocyte expression of lymphoid tissue-specific homing receptors, which are complementary for vascular addressins on high endothelial venules present in Peyer's patches and peripheral lymph nodes, provide a biochemical means for selectivity to this recirculation process (id.). Non-activated lymphocytes can move freely between mucosal and nonmucosal lymphoid tissues due to the presence of both types of homing receptors on their plasma membranes (Pals et al. (1989). *Immunol. Rev.* 108:111). Effector lymphocytes, and antigen-activated immunoblasts which are stimulated in a particular site in the body, however, exhibit a far more selective migratory behavior. These cells move primarily to tissues originally involved in antigen exposure and cellular activation (Hamann et al., supra; Pals et al., supra).

An immune response is initiated following T cell recognition of antigen peptides in the context of self MHC molecules, and generally takes place in one of the host's secondary lymphoid compartments. Cellular activation is triggered by the binding of antigen to the T cell receptor (TCR), forming an antigen/TCR complex which transduces the antigen-specific extracellular stimulation across the plasma membrane, and generates intracellular signals which include the activation of protein kinase C and the increases in intracellular calcium. While signal transduction can lead to T cell unresponsiveness, positive signal transduction events trigger a series of additional biochemical processes. One consequence of this activation is the stimulated production of a number of biologically active molecules, which are collectively termed lymphokines. (See, Alcover et al. (1987). *Immunol. Rev.* 95:5; Gelfand et al. (1987). *Immunol. Rev.* 95:59).

Vaccines are preparations of antigenic material for administration to induce in the recipient an immunity to infection or intoxication by a given infecting agent. Vaccines may be prepared from viruses, rickettsiae, bacteria, protozoa and metazoa. Vaccines may be sterile suspensions of the killed organisms, of toxoids or other antigenic material derived from the organisms or recombinant sources, which can be administered by injection. Vaccines may be either simple vaccines prepared from one species of organism or a variety of organisms, or they may be mixed vaccines containing two or more simple vaccines. They are prepared in such a manner as not to destroy the antigenic material, although the methods of preparation vary, depending on the vaccine.

Vaccine adjuvants consist of agents that are included in the formulation that are used to enhance the ability of the antigenic material in a vaccine to induce the desired immune response, and with many poorly antigenic materials the success of vaccination depends on the presence of a suitable adjuvant in the vaccine. The adjuvant is some- times conveniently incorporated in the vaccine before the latter is distributed into containers, although it may be provided in a separate container for mixing with the antigenic material when the vaccine is required for use in immunizing the recipient.

U.S. Pat. No. 4,698,221 discloses a vaccine which contains (a) an antigen, (b) a fat-soluble vitamin, such as Vitamin A, Vitamin D and/or Vitamin E, (c) a zinc compound, and (d) a selenium compound.

DHEA is a steroid hormone that has been extensively studied for many years. It has been reported to be involved in a wide variety of physiologic, immunologic, and pathologic conditions (for reviews, see Regelson et al. (1988). *Ann. N.Y. Acad. Sci.* 521:260; Gordon et al. (1986). *Adv. Enzyme Reg.* 26:355–382). Most endocrinologists believe that the primary function of DHEA is to serve as a precursor for the synthesis of testosterone and the estrogens by the gonads. Prior to its release into the bloodstream, the vast majority of newly synthesized DHEA becomes sulfated. The conjugated steroid DHEA-S is a secretory product of the adrenal gland in humans and certain primates. DHEA-S represents the major steroid hormone in the circulation of humans, and is converted to DHEA by the enzymatic activity of a steroid sulfatase.

Therapeutic uses for DHEA and certain analogs have been reported for diabetes, dry skin, ocular hypertension, obesity, and retroviral infections. Illustrative of these reports are the disclosures of U.S. Pat. No. 4,395,408, U.S. Pat. No. 4,518,595, U.S. Pat. No. 4,542,129, U.S. Pat. No. 4,617,299, U.S. Pat. No. 4,628,052, U.S. Pat. No. 4,666,898, published European Patent Application No. 0 133 995 A2, and published United Kingdom Patent Application No. GB 2 204 237 A.

SUMMARY OF THE INVENTION

The invention relates to a vaccine which comprises an antigen and an immune response augmenting agent. The immune response augmenting agent enhances production of IL-2, IL-3, IFN-γ or GM-CSF in T cells. Suitable immune response augmenting agents include, but are not limited to, DHEA, DHEA congeners and DHEA-derivatives.

The invention also relates to a method for enhancing an antigen-specific circulating antibody immune response which comprises administering a vaccine which comprises an antigen and an immunomodulator. The immunomodulator may be an immune response augmenting agent, a lymphoid organ modifying agent or a mixture of the immune response augmenting agent and lymphoid organ modifying agent. Suitable lymphoid organ modifying agents enhance the production of IL-4, IL-5 or IL-10 in T cells. Such agents include, but are not limited to, 1,25-dihydroxy Vitamin $D_3$ (1,25$(OH)_2D_3$), 25-hydroxy Vitamin $D_3$ (25$(OH)D_3$), biologically active 1,25$(OH)_2D_3$ derivatives which are capable of activating the intracellular Vitamin $D_3$ receptor, all trans-retinoic acid, retinoic acid derivatives, retinol and glucocorticoid. Alternatively, the method for enhancing an antigen-specific circulating antibody immune response comprises separately administering the immunomodulator and a vaccine containing an antigen.

BRIEF DESCRIPTION OF THE DRAWINGS

FIG. 13A shows the serum IgG response.

FIG. 13B shows the serum IgA response.

FIG. 13C shows the mucosal IgG response.

FIG. 13D shows the mucosal IgA response.

FIG. 14A shows the serum IgG response.

FIG. 14B shows the serum IgA response.

FIG. 14C shows the mucosal IgG response.

FIG. 14D shows the mucosal IgA response.

FIG. 15A shows the serum IgG response.

FIG. 15B shows the serum IgA response.

FIG. 15C shows the mucosal IgG response.

FIG. 15D shows the mucosal IgA response.

FIG. 16A shows the IgM response.

FIG. 16B shows the IgG response.

FIG. 16C shows the IgA response.

DETAILED DESCRIPTION OF THE INVENTION

Figure 1:
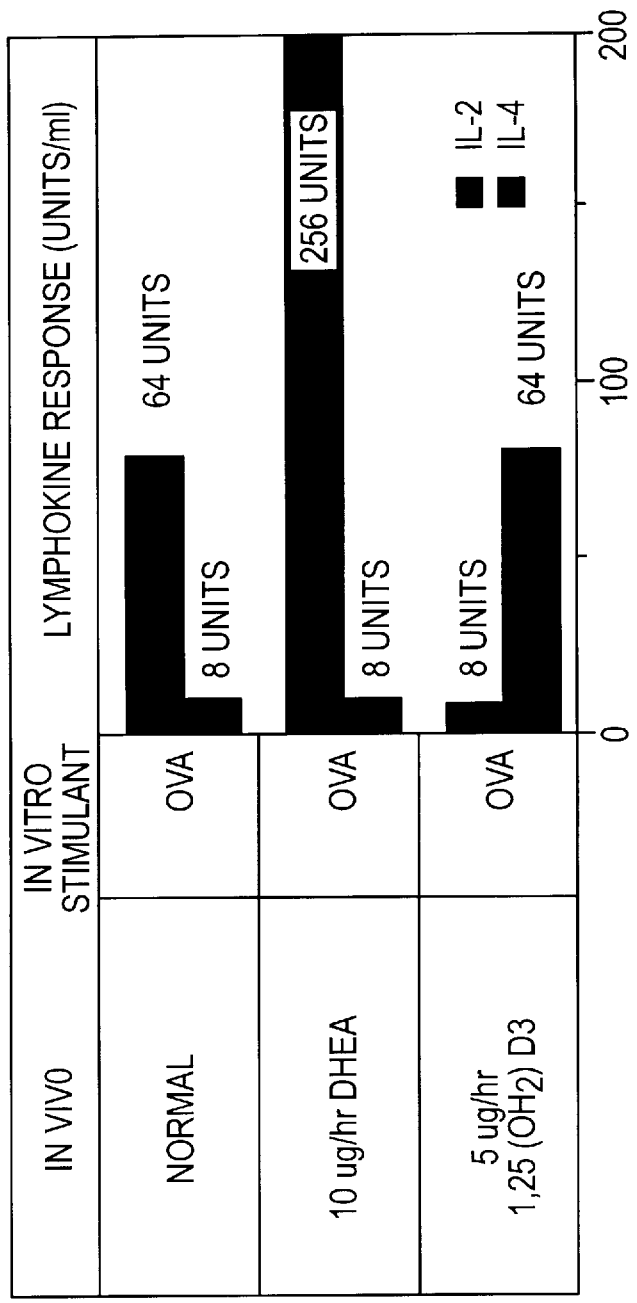
FIG. 1 is a graph showing the effect of DHEA and 1,25$(OH)_2D_3$ administered in vivo on lymphokine production by activated splenocytes.

The most important function of the immune system is to provide its host with protection against diseases. To carry out these tasks, a large and diverse array of effector mechanisms have evolved, the majority of which exhibit antigen specificity. Each individual effector mechanism possesses a degree of uniqueness with respect to its ability to influence the rate of progression, to detoxify, or to promote the elimination of microbial pathogens or tumor cells. Such a diversity in available mechanisms is absolutely essential, since no single effector response can effectively deal with all forms of pathogenic insults. Furthermore, to protect normal function of the various non-lymphoid organ systems and tissues of the body requires careful selection, activation, and compartmentalization of the most appropriate types of immune effector mechanisms. Equally important is the simultaneous capacity to down-regulate the development of other types of responses. Immunologic effector responses must, therefore, be both effective and practical, and at the same time be appropriately regulated anatomically to reduce the risk of pathologic consequences.

The non-lymphoid tissues and organs of the body, which work collectively to sustain the life of the host, must also be capable of providing regulatory information to cells of the immune system. This information, mediated through the activities of inflammation-induced tissue cytokines, prostaglandins and other types of biological response modifiers, becomes integrated into the complex equation to control the mechanisms which regulate effector response selection.

T cells, through their capacity to produce a number of lymphokines in response to activation, play a central role in guiding the development of immune effector responses. Mechanisms which operate to control the synthesis and secretion of these pleiotropic biologic response modifiers, therefore, directly influence the quantitative and qualitative nature of immunity. The lymphokines and cytokines provide important information, not only to cells of the immune system, but also to cells of the other tissue and organ systems. For this information to be meaningful, it is essential that lymphokine production remains tightly controlled at the levels of both cellular source and duration. Autocrine and paraerine effects by lymphokines and cytokines should be the norm, since only a few species are capable of working effectively when provided via endocrine routes. These essential anatomic restrictions, therefore, cannot be adequately provided by bolus injection of recombinant lymphokines and/or cytokines, and may explain the limited success associated with this form of therapy.

The vast majority of the T cells in the peripheral circulation are known to reside within the recirculating T cell pool. These cells continuously enter and exit secondary lymphoid organs throughout the body, maintaining residence within any particular site for only finite periods of time. Over the lifespan of any individual mature T cell, therefore, it has probably taken up temporary residence in most of a host's secondary lymphoid organs. T cell recirculation provides the immune system with a means for clonally-restricted T cells to provide a level of surveillance over all of the tissue and organ systems.

It is universally accepted that most T cells acquire their specificity for antigen, and for a self-MHC-restricting element, during processes which occur at the time of their ontogeny within the thymus. However, the extent to which intrathymic maturation confers genetic restrictions upon individual T cells that regulate their potential for immunologic involvement has not been delineated.

A general concept which explains the results in the Examples, but which is not intended to limit the invention, is that the genetic programs of resting recirculating T cells are continuously being altered by extrinsic environmental influences. The steroid hormones, either presented systemically in their active forms (e.g., as glucocorticosteroids (GCS)), or provided to T cells only within discrete microenvironments as a consequence of end-organ metabolism (e.g., as DHEA, DHT or $1,25(OH)_2D_3$), perform important roles in this process. The basal regulation of the immune system at the level of the T cell requires the continual presence of the needed substrates (prohormones). The anatomic compartmentalization of functional potential for T cells, therefore, would be dependent on the cellular source of the steroid metabolizing enzymes able to convert the steroid hormone substrates to their bioactive products. It has been shown that macrophages can contain each of these enzymes.

More specifically, DHEA-S can be naturally converted to DHEA in the peripheral lymph nodes of animals with normal immune function. The DHEA produced then influences the T lymphocytes within the lymph node and exerts controlling influences on their ability to respond when activated. This provides a means to regulate the potential of T cells by fluctuating the degree to which a particular steroid hormone exists within a particular tissue. Old individuals and/or stressed individuals, including humans, have a reduced capacity to produce DHEA-S, resulting in altered T-cell responsiveness. The invention in its various embodiments restores the metabolite produced from DHEA-S in the anatomic compartment in which appropriate T-cell responsiveness is required for normal immune responses to T-cell-dependent antigens.

The invention relates to a vaccine which comprises an antigen and an immune response augmenting agent. The immune response augmenting agent enhances production of IL-2, IL-3, IFN-γ or GM-CSF in T cells. Suitable immune response augmenting agents include, but are not limited to, DHEA, DHEA congeners and DHEA-derivatives.

The invention also relates to a method for enhancing an antigen-specific circulating antibody immune response which comprises administering a vaccine which comprises an antigen and an immunomodulator. The immunomodulator may be an immune response augmenting agent, a lymphoid organ modifying agent or a mixture of the immune response augmenting agent and lymphoid organ modifying agent. Suitable lymphoid organ modifying agents enhance the production of IL-4, IL-5 or IL-10 in T cells. Such agents include, but are not limited to, 1,25-dihydroxy Vitamin $D_3$ ($1,25(OH)_2D_3$), 25-hydroxy Vitamin $D_3$ ($25(OH)D_3$), biologically active $1,25(OH)_2D_3$ derivatives which are capable of activating the intracellular Vitamin $D_3$ receptor, all trans-retinoic acid, retinoic acid derivatives, retinol and glucocorticoid. Alternatively, the method for enhancing an antigen-specific circulating antibody immune response comprises separately administering the immunomodulator and a vaccine containing an antigen.

As used herein, the term "immunomodulator" refers to an agent which is able to modulate an immune response. An example of such modulation is an enhancement of antibody production.

The term "individual" refers to a vertebrate and preferably to a member of a species which naturally produces DHEA and DHEA-S and possesses DHEA-S sulfatase activity, and includes, but is not limited to domestic animals, sports animals and primates, including humans.

The term "effective amount" of an immunomodulator refers to an amount of an immunomodulator sufficient to enhance a vaccine-induced humoral immune response. An effective amount of an immunomodulator, if injected, can be in the range of about 0.1–1,000 μg, preferably 1–900 μg, more preferably 5–500 μg, for a human subject, or in the range of about 0.01–10.0 μg/Kg body weight of the subject animal. This amount may vary to some degree depending on the mode of administration, but will be in the same general range. If more than one immunomodulator is used, each one may be present in these amounts or the total amount may fall within this range.

An effective amount of an antigen may be an amount capable of eliciting a demonstrable humoral immune response in the absence of an immunomodulator. For many antigens, this is in the range of about 5–100 μg for a human subject. Since the vaccines of the invention utilize an immunomodulator which enhances the humoral immune response, it may be possible to utilize less antigen, e.g., about 1–5 μg for a human subject. The appropriate amount of antigen to be used is dependent on the specific antigen and is well known in the art.

The exact effective amount necessary will vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the vaccine art.

"Treatment" refers to the administration to an individual of a composition which yields a protective immune response, and includes prophylaxis and/or therapy.

An "antigen" refers to a molecule containing one or more epitopes that will stimulate a host's immune system to make a secretory, humoral and/or cellular antigen-specific response, or to a DNA molecule which is capable of producing such an antigen in a vertebrate. The term is also used interchangeably with "immunogen."

The specific antigen can be a protein, a polysaccharide, a lipopolysaccharide or a lipopeptide; or it can be a combination of any of these. Particularly, the specific antigen can include a native protein or protein fragment, or a synthetic protein or protein fragment or peptide; it can include glycoprotein, glycopeptide, lipoprotein, lipopeptide, nucleoprotein, nucleopeptide; it can include a peptide-peptide conjugate; or it can include a recombinant nucleic acid expression product. The antigen may further be a DNA molecule which produces an antigen in the vertebrate. Examples of antigens include, among others, those that are capable of eliciting an immune response against viral or bacterial hepatitis, influenza, diphtheria, tetanus, pertussis, measles, mumps, rubella, polio, pneumococcus, herpes, respiratory syncytial virus, haemophilus influenza type b, chlamydia, varicella-zoster virus or rabies.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

By "vaccine composition" or "vaccine" is meant an agent used to stimulate the immune system of an individual so that current harm is alleviated, or protection against future harm is provided.

"Immunization" refers to the process of inducing a continuing protective level of antibody and/or cellular immune response which is directed against an antigen to which the organism has been previously exposed.

A "pharmacologic dose" is one which gives a desired physiological effect.

An "immune response augmenting agent", as used herein, means an agent that is capable, when administered to a vertebrate animal in vivo, of restoring T cell responsiveness to T cell dependent antigens characteristic of normal immune responses to such antigens. Immune response augmenting agents are capable of enhancing T cell production of IL-2, IL-3, IFN-γ or GM-CSF. By way of example, the immune response augmenting agent can be a substance such as DHEA, DHEA congener or a DHEA-derivative (collectively referred to herein as DHEA congener). A DHEA congener is a compound related to DHEA, such as a derivative. Suitable substances can be readily identified by screening for enhanced IL-2, IL-3, IFN-γ or GM-CSF production by T cells as described in Ser. No. 07/779,499.

Examples of "DHEA", "DHEA congener" or "DHEA-derivative", include but are not limited to, compounds having the formula

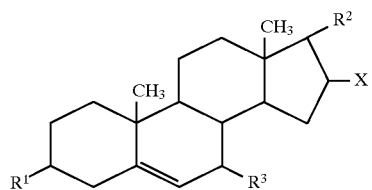

wherein
X is H or halogen;
$R^1$, $R^2$ and $R^3$ are independently =O, —OH, —SH, H, halogen, pharmaceutically I acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$;
$R^5$ and $R^6$ are independently —OH, pharmaceutically acceptable esters or pharmaceutically acceptable ethers; and
pharmaceutically acceptable salts Thus, examples of suitable DHEA congeners include compounds in which:

(1) $R^2$ is =O, $R^3$ and X are each H and $R^1$ is =O, —OH, pharmaceutically acceptable esters thereof, pharmaceutically acceptable ethers thereof or pharmaceutically acceptable salts;

(2) $R^2$ is =O, $R^3$ is H, X is halogen and $R^1$ is =O, —OH, pharmaceutically acceptable esters thereof, pharmaceutically acceptable ethers thereof or pharmaceutically acceptable salts;

(3) $R^2$ is =O, $R^3$ and X are each H and $R^1$ is —SH, pharmaceutically acceptable thioesters thereof, pharmaceutically acceptable thioethers thereof or pharmaceutically acceptable salts;

(4) $R^2$ is =O, $R^3$ is H, X is halogen and $R^1$ is —SH, pharmaceutically acceptable thioesters thereof, pharmaceutically acceptable thioethers thereof or pharmaceutically acceptable salts;

(5) $R^2$ is =O, X is H and $R^1$ and $R^3$ are independently =O, —OH, pharmaceutically acceptable esters thereof, pharmaceutically acceptable ethers thereof or pharmaceutically acceptable salts;

(6) $R^2$ is =O, X is halogen and $R^1$ and $R^3$ are independently =O, —OH, pharmaceutically acceptable esters thereof, pharmaceutically acceptable ethers thereof or pharmaceutically acceptable salts;

(7) $R^2$ is =O, X is H and RI and $R^3$ are independently —SH, pharmaceutically acceptable thioesters thereof, pharmaceutically acceptable thioethers thereof or pharmaceutically acceptable salts;

(8) $R^2$ is =O, X is halogen and $R^1$ and $R^3$ are independently —SH, pharmaceutically acceptable thioesters thereof, pharmaceutically acceptable thioethers thereof or pharmaceutically acceptable salts;

(9) $R^2$ is —OH, $R^3$ and X are each H and R is =O, —OH, pharmaceutically acceptable esters thereof, pharmaceutically acceptable ethers thereof or pharmaceutically acceptable salts;

(10) $R^2$ is —OH, $R^3$ is H, X is halogen and $R^1$ is =O, —OH, pharmaceutically acceptable esters thereof, pharmaceutically acceptable ethers thereof or pharmaceutically acceptable salts;

(11) $R^2$ is —OH, $R^3$ and X are each H and $R^1$ is —SH, pharmaceutically acceptable thioesters thereof, pharmaceutically acceptable thioethers thereof or pharmaceutically acceptable salts;

(12) $R^2$ is —OH, $R^3$ is H, X is halogen and $R^1$ is —SH, pharmaceutically acceptable thioesters thereof, pharmaceutically acceptable thioethers thereof or pharmaceutically acceptable salts;

(13) $R^2$ is —OH, X is H and $R^1$ and $R^3$ are independently =O, —OH, pharmaceutically acceptable esters thereof, pharmaceutically acceptable ethers thereof or pharmaceutically acceptable salts;

(14) $R^2$ is —OH, X is halogen and $R^1$ and $R^3$ are independently =O, —OH, pharmaceutically acceptable esters thereof, pharmaceutically acceptable ethers thereof or pharmaceutically acceptable salts;

(15) $R^2$ is —OH, X is H and $R^1$ and $R^3$ are independently —SH, pharmaceutically acceptable thioesters thereof, pharmaceutically acceptable thioethers thereof or pharmaceutically acceptable salts;

(16) $R^2$ is —OH, X is halogen and $R^1$ and $R^3$ are independently —SH, pharmaceutically acceptable thioesters thereof, pharmaceutically acceptable thioethers thereof or pharmaceutically acceptable salts;

(17) $R^2$ is —SH, $R^3$ and X are each H and $R^1$ is =O, —OH, pharmaceutically acceptable esters thereof, pharmaceutically acceptable ethers thereof or pharmaceutically acceptable salts;

(18) $R^2$ is —SH, $R^3$ is H, X is halogen and $R^1$ is =O, —OH, pharmaceutically acceptable esters thereof, pharmaceutically acceptable ethers thereof or pharmaceutically acceptable salts;

(19) $R^2$ is —SH, $R^3$ and X are each H and $R^1$ is —SH, pharmaceutically acceptable thioesters thereof, pharmaceutically acceptable thioethers thereof or pharmaceutically acceptable salts;

(20) $R^2$ is —SH, $R^3$ is H, X is halogen and $R^1$ is —SH, pharmaceutically acceptable thioesters thereof, pharmaceutically acceptable thioethers thereof or pharmaceutically acceptable salts;

(21) $R^2$ is —SH, X is H and $R^1$ and $R^3$ are independently =O, —OH, pharmaceutically acceptable esters thereof, pharmaceutically acceptable ethers thereof or pharmaceutically acceptable salts;

(22) $R^2$ is —SH, X is halogen and $R^1$ and $R^3$ are independently =O, —OH, pharmaceutically acceptable esters thereof, pharmaceutically acceptable ethers thereof or pharmaceutically acceptable salts;

(23) $R^2$ is —SH, X is H and $R^1$ and $R^3$ are independently —SH, pharmaceutically acceptable thioesters thereof, pharmaceutically acceptable thioethers thereof or pharmaceutically acceptable salts;

(24) $R^2$ is —SH, X is halogen and $R^1$ and $R^3$ are independently —SH, pharmaceutically acceptable thioesters thereof, pharmaceutically acceptable thioethers thereof or pharmaceutically acceptable salts;

(25) X is H and $R^1$, $R^2$ and $R^3$ are independently =O, —OH, a sugar residue, pharmaceutically acceptable esters thereof or pharmaceutically acceptable ethers thereof or pharmaceutically acceptable salts, wherein at least one of $R^1$, $R^2$ and $R^3$ is a sugar residue;

(26) X is halogen and $R^1$, $R^2$ and $R^3$ are independently =O, —OH, a sugar residue, pharmaceutically acceptable esters thereof, pharmaceutically acceptable ethers thereof or pharmaceutically acceptable salts, wherein at least one of $R^1$, $R^2$ and $R^3$ is a sugar residue;

(27) X is H and $R^1$, $R^2$ and $R^2$ are independently =O, —OH, pharmaceutically acceptable inorganic esters thereof or pharmaceutically acceptable salts, wherein at least one of $R^1$, $R^2$ and $R^3$ is an inorganic ester;

(28) X is halogen and $R^1$, $R^2$ and $R^3$ are independently =O, —OH, pharmaceutically acceptable inorganic esters thereof or pharmaceutically acceptable salts, wherein at least one of $R^1$, $R^2$ and $R^3$ is an inorganic ester.

Pharmaceutically acceptable esters or thioesters include, but are not limited to, esters or thioesters of the formula —OOCR or —SOCR, wherein R is a pharmaceutically acceptable alkyl, alkenyl, aryl, alkylaryl, arylalkyl, spingosine or substituted spingolipid groups, such as propionate, enanthate, cypionate, succinate, decanoate and phenylpropionate esters.

Pharmaceutically acceptable ethers or thioethers include, but are not limited to, ethers or thioethers of the formula —OR or —SR, wherein R is as defined above or enol, or —$OR^4$ is an unsubstituted or substituted spirooxirane or —SR is a spirothiane.

Suitable sugar residues include, but are not limited to monosaccharides, disaccharides and oligosaccharides, such as a glucuronate.

Pharmaceutically acceptable inorganic esters include, but are not limited to, inorganic esters of the formula —$OSO_2R^5$ or —$OPOR^5R^6$, wherein $R^5$ and $R^6$ are independently —OH, pharmaceutically acceptable esters, pharmaceutically acceptable ethers or pharmaceutically acceptable salts.

"Lymphoid organ modifying agent", as used herein, means a modifier that is capable, when administered to a vertebrate animal in vivo at a peripheral site, of altering the microenvironment of a peripheral lymphoid organ that drains from the administration site, such that activated lymphocytes and macrophages residing within the lymphoid organ exhibit a pattern of cytokines more typical of the microenvironment of a lymphoid organ of the mucosal lymphoid compartment. Particularly, a pattern of cytokines more typical of a mucosal lymphoid organ is characterized by relatively enhanced production of one or more of active TGF-β, IL-4, IL-5, and IL-10, and relatively decreased production (or at least no relatively enhanced production) of one or more of IL-2 and IFN-γ. In preferred embodiments, the lymphoid organ modifying agent includes a biological response modifier that can, or a combination of biological response modifiers that together can, when administered to a peripheral lymph organ, result in the lymphoid organ exhibiting a pattern of cytokines more typical of a mucosal lymphoid organ. By way of example, it can be a substance known to enhance or facilitate production of active TGF-β, such as, for example, retinoic acid, retinoic acid derivatives, retinol or retinol derivatives; or it can be 1,25$(OH)_2D_3$, 25$(OH)D_3$ or biologically active 1,25$(OH)_2D_3$ derivatives; or glucocorticoids. Biologically active 1,25$(OH)_2D_3$ derivatives are those derivatives which are capable of activating the intracellular Vitamin $D_3$ receptor. Suitable derivatives can thus be readily identified by screening for activation of the intracellular Vitamin $D_3$ receptor (Minghetti and Norman (1988). *FASEB J.* 2:3043–3053). Alternatively, suitable derivatives can be readily identified by screening for enhanced IL-4 production by T cells as described in Ser. No. 07/779,499. Examples of suitable biologically active Vitamin $D_3$ derivatives include, but are not limited to, 1,25-dihydroxy-16-ene Vitamin $D_3$ and calcipotriene. Preferably, the lymphoid organ modifying agent is administered epicutaneously at a peripheral anatomical site (such as, for human subjects, for example, the arm or buttocks or leg); and the specific antigen is administered to the same anatomical site, or to a site known to drain into the same lymphoid organ that receives drainage from the site of administration of the lymphoid organ modifying agent. In one mode of administration, the lymphoid organ modifying agent can be combined with the specific antigen and immune response augmenting agent for simultaneous administration at the same site. The lymphoid organ modifying agent, the specific antigen and immune response augmenting agent, or all of them, can be administered by injection.

The practice of the present invention will employ, unless otherwise indicated, conventional techniques of molecular biology, microbiology, biochemistry, and immunology, which are within the skill of the art. Such techniques are explained fully in the literature. See, e.g., *ANIMAL CELL CULTURE* (R. I. Freshney, Ed. 1986); *IMMOBILIZED CELLS AND ENZYMES* (IRL Press, 1986); the series, *METHODS IN ENZYMOLOGY* (Academic Press, Inc.), *IMMUNOCHEMICAL METHODS IN CELL AND MOLECULAR BIOLOGY* (Academic Press, London), Scopes, (1987); and *HANDBOOK OF EXPERIMENTAL IMMUNOLOGY*, Volumes I–IV, (D. M. Weir and C. C. Blackwell, Eds., 1986). All patents, patent applications and publications mentioned herein, both supra and infra, are incorporated herein by reference.

The simultaneous enhancement or maximization of the production of more than one T cell lymphokine may be achieved by exposing the T cell lymphocyte to more than one immunomodulator prior to cellular activation. The exposure to more than one immunomodulator can be simultaneous or sequential. The concentration of each of the immunomodulators should be balanced to achieve the desired enhancing effects on the vaccine-induced humoral immune response.

Evidence derived from experimental and clinical observations indicates that immunologic reactions elicited to either simple or complex antigens often manifest as a balanced heterogenous blend of both cellular and humoral components, with the fractional contribution of any individual type of effector mechanism often dominating the overall response. This level of heterogeneity is essential to the development of a protective immune response. Alterations to this natural balance, whether caused by genetic or physiologic changes associated with age or stress or trauma, can lead to a depressed capacity to elicit protective immune responses, and might also lead to immunologic responses having pathologic consequences.

Pharmaceutical compositions made up of formulations comprised of the immunomodulators and suitable for administration by subcutaneous, epicutaneous, topical, intramuscular or intradermal routes and the like may be prepared by one of ordinary skill in the art. See, for example, *Remington's Pharmaceutical Sciences*, 17th Ed. (1985, Mack Publishing Co., Easton, Pa.). For example, the pharmaceutical composition containing the immunomodulator may also contain a physiologically acceptable carrier that is non-toxic to the treated animal and is compatible with the steroid. Suitable pharmaceutical carriers include liquid carriers, such as normal saline and other non-toxic salts at or near physiological concentrations.

The pharmaceutical composition containing the immunomodulator is used as a vaccine adjuvant to enhance a vaccine-induced humoral immune response. When the individuals are immunized with an immunizing agent, administration of the immunomodulator may be prior to, contemporaneously with, or after the vaccination. Typical methods of administering the immunomodulator include mixing the immunomodulator with the immunizing agent (antigen) in a vaccine or topically applying the immunomodulator to skin sites which drain into the same lymph nodes as the antigen of the vaccine. This latter method is preferably used with individuals who are immunologically deficient due to low levels of DHEA-S and/or DHEA and in whom one wishes to augment the immune response, for example, the aged or neonates or individuals who are therapeutically immunosuppressed.

One or more immunomodulators may be used to enhance the vaccine-induced immune response. They may be administered sequentially or contemporaneously. It is preferred to administer them contemporaneously and in a single vehicle. It has been discovered that a synergistic enhancing effect is achieved when an immune response augmenting agent, as defined herein, is combined with a lymphoid organ modifying agent, as defined herein, and used as the immunomodulator. It is preferred to include the two agents in the vaccine, although either or both may also be topically applied. In general, an effective amount of immunomodulator may be about 0.1–1,000 μg, preferably 1–900 μg, and more preferably 5–500 μg, for a human subject. An effective amount of an immune response augmenting agent may be about 10–1,000 μg, preferably 10–900 μg, more preferably 10–500 μg, and most preferably 20–200 μg, for a human subject if administered by injection. If the immune response augmenting agent is administered orally, the amount may range from about 10–100 mg/day, preferably 20–50 mg/day, for a human subject, or in the range of about 0.5–5 mg/Kg/day for an animal subject. An effective amount of a lymphoid organ modifying agent may be about 0.1–500 μg, preferably 0. 1–400 μg, and more preferably 0.5–250 μg, for a human subject.

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLE 1

The Effect of DHEA and 1,25(OH)$_2$D$_3$ in vivo on IL-2 and IL-4 Production in vitro C3H mice received implants of biodegradable DHEA or 1.25(OH)$_2$D$_3$ pellets designed to deliver steroid at a rate of 10.4 and 2.6 μg/hour, respectively. Three days after implantation, both the steroid treated groups of mice and a normal control group were immunized in the hind footpads with 100 μg OVA in CFA. Ten days after immunization, the draining lymph nodes and spleens from all groups were prepared for culture. Lymph node cells were stimulated with 100 μg OVA. Culture supernatants were assayed for IL-2 and IL-4 activity after 24 hours using the HT-2 bioassay. The results are shown in FIG. 1. From the Figure, it is seen that DHEA administration caused an approximately four-fold increase in IL-2 production, and no stimulation of IL-4 production. In contrast, 1,25(OH)$_2$D$_3$ administration caused an approximately eight-fold increase in IL-4 production, but did not stimulate IL-2 production.

Similar alterations in the ability of antigen-activated T cells to produce IL-2 and IL-4 were observed when the immune response augmenting agent was mixed with the immunizing antigen, or was topically applied to skin sites above the site of vaccination.

EXAMPLE 2

Preservation of Normal Potential to Produce T-cell Lymphokines and Generate Humoral Immune Responses by Supplementation with DHEA Sulfate Circulating levels of DHEA sulfate decline markedly with advancing age in humans and other mammals. As shown in application U.S. Ser. No. 07/779,499, direct treatment of T cells from aged or normal murine donors with DHEA prior to activation in vitro augmented their capacity to produce IL-2. In contrast, DHEA-S, the prohormone form of DHEA found principally in the circulation, was shown to have no direct effect on T-cell production of this lymphokine. When DHEA-S was administered to normal mature adults in vivo, it enhanced the potential for IL-2 production by T cells isolated from lymphoid organs having the greatest DHEA-S activity. The most active lymphoid organs are those having anatomic positions downstream of nonmucosal tissues. This Example demonstrates that DHEA-S supplementation in vivo can influence the age-related changes in lymphokine production and humoral immune responses.

Groups of adult BALB/c mice, between 35 and 39 weeks of age, were separated into two groups. One group was provided with 100 μg/ml DHEA-S in their drinking water. The hormone was offered ad libitum to these animals. The other group was left untreated. Mice were maintained on oral DHEA-S supplementation until age 114 weeks, when they were sacrificed and their spleens individually analyzed for the capacity to produce lymphokines following anti-$CD_3\epsilon$ activation. The DHEA-S treated and untreated mice were evaluated by comparing their responses to the lymphokine profile produced by similarly activated splenocytes from mature adult mice (13 weeks of age).

More specifically, splenocytes were prepared from the following groups of BALB/c mice; 2 mature adult (13 weeks), 2 aged (114 weeks), and 2 aged (114 weeks) receiving 100 μg/ml DHEA-S in their drinking water for the previous 61 weeks. $1 \times 10^7$ splenocytes were cultured under serum-free conditions in triplicate and activated with 1 μg/ml $CD_3\epsilon$. Culture supernatants were analyzed for the level of IL-2 by a quantitative bioassay, and for IL-4, IL-5, γ-IFN, IL-3 and GM-CSF by capture ELISA.

FIGS. 2A–2F are graphs showing the results of DHEA-S supplementation on the capacity of T cells to produce a variety of lymphokines. In FIGS. 2A–2F, bars represent the mean ±SD for the value of each lymphokine presented. It is seen from FIGS. 2A–2F that DHEA-S supplementation, administered prior to the onset of age-induced decline in immunocompetence, is accompanied by the preservation of normal lymphokine production and development of normal humoral immune responses. DHEA-S supplementation was not only able to preserve normal levels of IL-2, IL-3, and GM-CSF production by activated T cells, but was also able to prevent age-related increase in γ-IFN, IL-4, and IL-5 production seen in the cell supernatants from untreated aged donors. The results of this study demonstrate that a striking correlation exists between the age-related decline in endogenous DHEA production (plus its metabolites) and the age-associated alterations in T-cell production of lymphokines.

The effect of DHEA-S supplementation on T cell function was also performed using BALB/c, C57BL/6 and C3H/HeN strains of mice. In each test of this experimental approach, lymphokine production by T cells from the treated aged donors had been preserved.

Figure 2A:
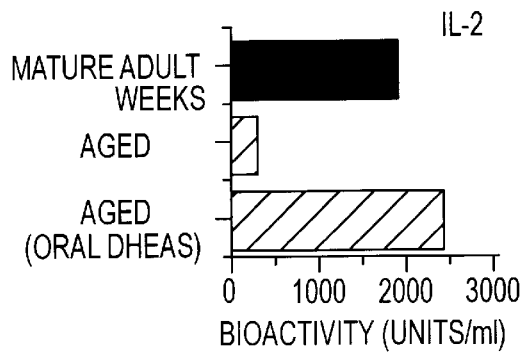
FIG. 2A is a graph showing the results of DHEA-S supplementation on the capacity of T cells from aged mice to produce IL-2.
Figure 2B:
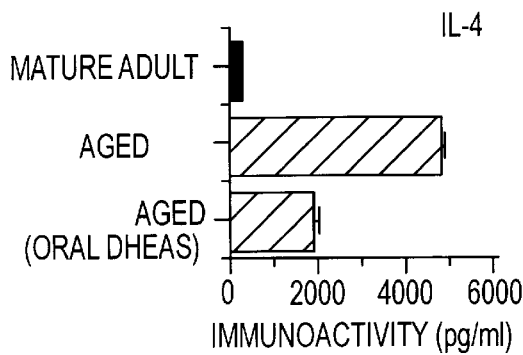
FIG. 2B is a graph showing the results of DHEA-S supplementation on the capacity of T cells from aged mice to produce IL-4.
Figure 2C:
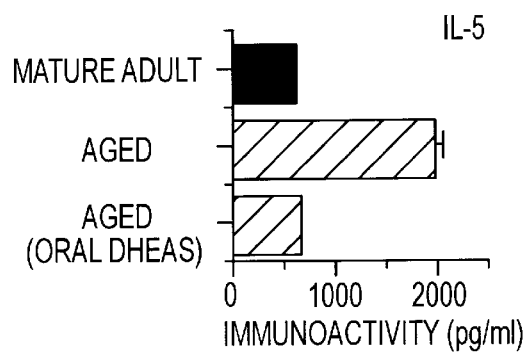
FIG. 2C is a graph showing the results of DHEA-S supplementation on the capacity of T cells from aged mice to produce IL-5.
Figure 2D:
FIG. 2D is a graph showing the results of DHEA-S supplementation on the capacity of T cells from aged mice to produce γIFN.
Figure 2E:
FIG. 2E is a graph showing the results of DHEA-S supplementation on the capacity of T cells from aged mice to produce GM-CSF.
Figure 2F:
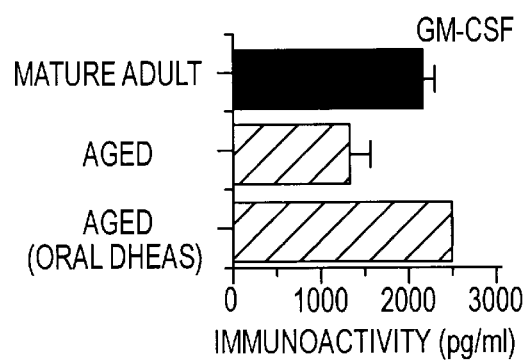
FIG. 2F is a graph showing the results of DHEA-S supplementation on the capacity of T cells from aged mice to produce IL-3.
Figure 2G:
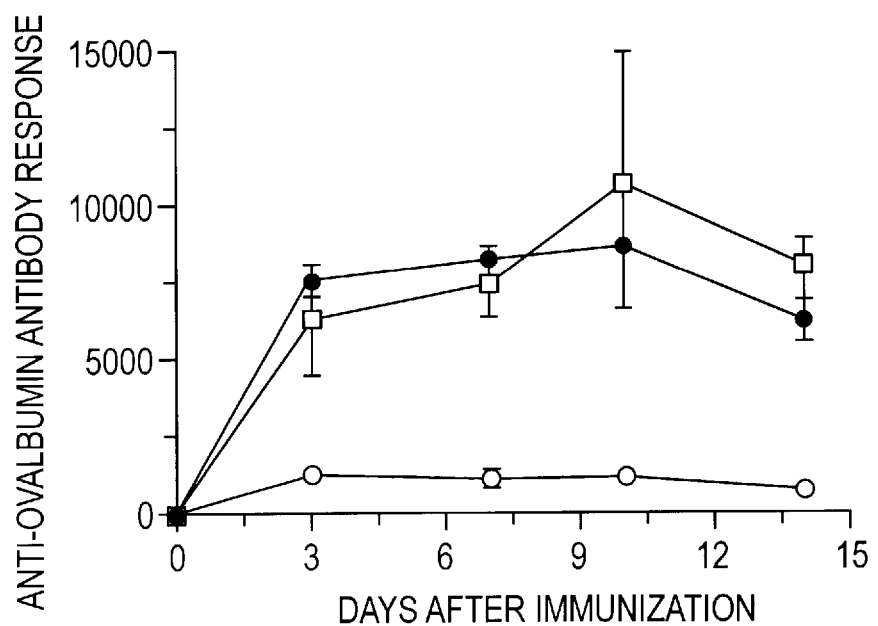
FIG. 2G is a graph showing the results of chronic DHEA-S supplementation on the humoral responsiveness of aged mice to an ovalbumin (OVA) challenge. The responsiveness is shown for mature adult mice (□), aged mice (○), and aged mice with oral DHEA-S (●).

In order to examine the effect of DHEA-S supplementation on the ability of old animals to mount immunologic responses to challenge with foreign protein antigens, the following procedure was used. Groups of 5 mature adult mice (13 weeks), 5 aged mice (114 weeks), and aged mice (114 weeks) provided with chronic DHEA-S supplementation (100 μg/ml DHEA-S in their drinking water for the previous 61 weeks, initiated at 8 months of age), were footpad-immunized with ovalbumin. The immunization was with 100 μg ovalbumin in a 25 μl volume of Maalox, administered in the hind footpads. All animals were bled on Days 0, 3, 5, 7, 10, and 14 post-immunization, and individual serum samples analyzed for ovalbumin specific antibody titres by quantitative ELISA, using ovalbumin for capture and HRPO-coupled, goat anti-murine Ig detecting antibodies with specificity for IgM and IgG sub-classes. Each ELISA assay was controlled with sera known to be positive or negative for anti-ovalbumin activity. The titre is the inverse of the antibody dilution equal to the half-maximal point on the titration curve. The results of the study, shown in the graph in FIG. 2G, demonstrate that old animals provided with chronic DHEA-S supplementation remain fully capable of rapidly mounting a significant humoral immune response to ovalbumin immunization, with kinetics, titres, and isotype profiles that are almost identical to mature adult controls. As expected, the untreated aged mice responded poorly to a similar antigen challenge, producing predominantly IgM.

EXAMPLE 3

DHEA-S Administration to Aged Mice Can Reverse Age-Associated Changes in T-cell Lymphokine Production and Their Depressed Humoral Immune Responses to Protein Antigens As shown in application U.S. Ser. No. 07/779,499, a direct exposure of lymphocytes from aged donors to DHEA in vitro immediately altered the pattern of lymphokines produced following activation. In addition, it has been found that nonmucosal tissue-draining lymphoid organs possess a far greater amount of DHEA sulfatase activity than mucosal tissue-draining lymphoid organs. These findings led to the hypothesis that DHEA may be serving as an effector of positional information for lymphocytes residing in certain lymphoid compartments. Any changes in immune function caused by the depressed production of substrate DHEA-S might, therefore, be reversible if DHEA-S is reintroduced in situ. This was examined in the following studies.

Splenocytes were isolated from equal-sized groups of mature adult mice (25 weeks), aged mice (120 weeks), and aged mice (120 weeks) given a subcutaneous injection of DHEA-S (100 μg in 100 μl propylene glycol) 24 hours previously. $1 \times 10^7$ splenocytes were cultured under serum-free conditions in triplicate and activated with 1 μg/ml anti-$CD_3\epsilon$. Twenty-four hours later, culture supernatants from individual cell cultures were analyzed for the level of IL-2 by a quantitative bioassay, and for IL-4, IL-5, γ-IFN, IL-3 and GM-CSF by capture ELISA. The results, shown in FIGS. 3A–3F, demonstrate that acute replacement therapy to aged mice with DHEA-S restores near-normal patterns of T-cell lymphokines within one day of treatment. These results strongly show that lymphoid cells from old animals exhibit no intrinsic defects. Rather, some of the best documented functional changes to the immune system which accompany aging are due to the reduced capacity to produce DHEA-S.

Figure 3A:
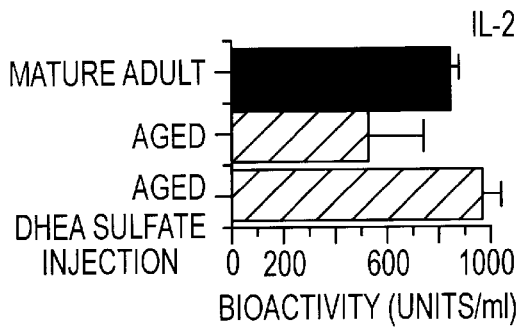
FIG. 3A is a graph showing the results of administration of a bolus of DHEA-S to aged mice on the ability of splenocytes from the treated mice to have restored IL-2 production.
Figure 3B:
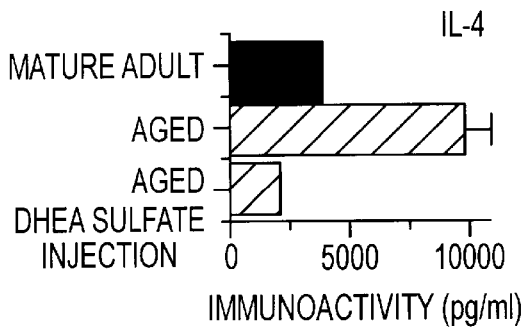
FIG. 3B is a graph showing the results of administration of a bolus of DHEA-S to aged mice on the ability of splenocytes from the treated mice to have restored IL-4 production.
Figure 3C:
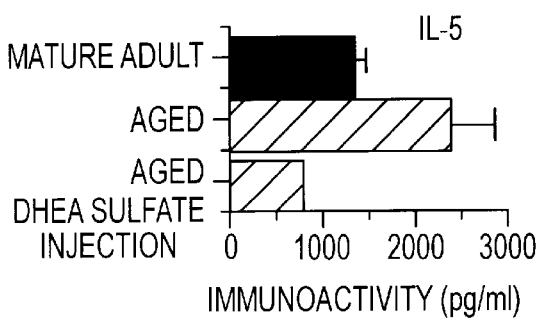
FIG. 3C is a graph showing the results of administration of a bolus of DHEA-S to aged mice on the ability of splenocytes from the treated mice to have restored IL-5 production.
Figure 3D:
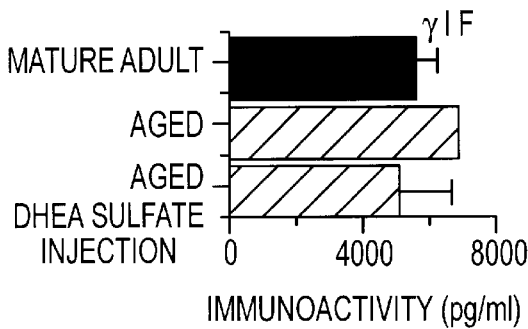
FIG. 3D is a graph showing the results of administration of a bolus of DHEA-S to aged mice on the ability of splenocytes from the treated mice to have restored γIFN production.
Figure 3E:
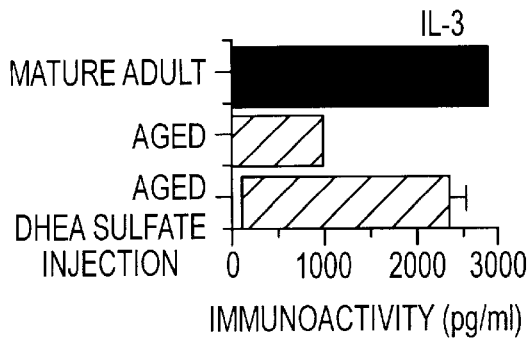
FIG. 3E is a graph showing the results of administration of a bolus of DHEA-S to aged mice on the ability of splenocytes from the treated mice to have restored IL-3 production.
Figure 3F:
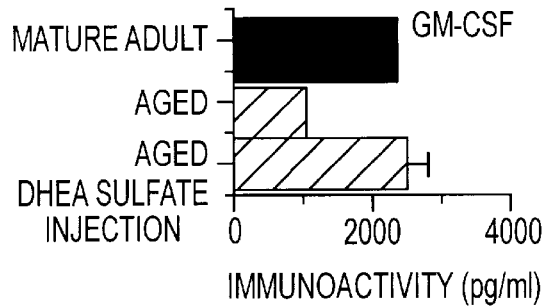
FIG. 3F is a graph showing the results of administration of a bolus of DHEA-S to aged mice on the ability of splenocytes from the treated mice to have restored GM-CSF production.
Figure 3G:
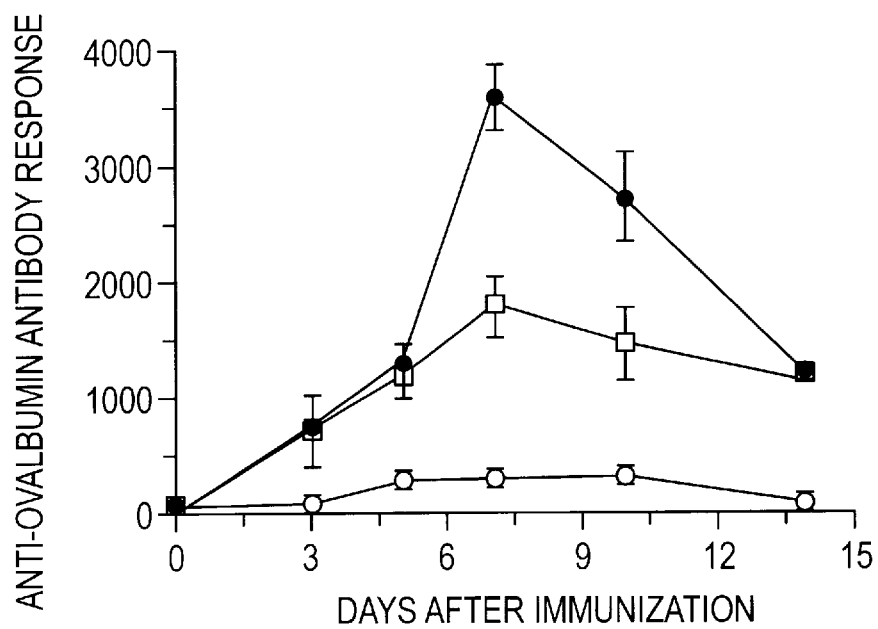
FIG. 3G is a graph showing the results of administration of a bolus of DHEA-S to aged mice on the production of anti-ovalbumin antibodies by the treated mice. The antibody production is shown for mature adult mice (□), aged mice (○), and aged mice with DHEA-S injection (●).

A representative study, showing that administration of a bolus of DHEA-S to aged BALB/c mice restored the capacity of the mice to develop humoral responses, is shown in FIG. 3G. In the study, groups of 5 mature adult (25 weeks), 5 aged (120 weeks), and 5 aged (120 weeks) mice receiving 100 μg DHEA-S in 100 μl propylene glycol by subcutaneous injection the previous 24 hours were immunized with 100 μg ovalbumin in a 25 μl volume of Maalox, administered in the hind footpads. Sera from individual mice were collected on Days 0, 3, 5, 7, 10 and 14 following primary immunization. The titre of anti-ovalbumin antibody was assessed by ELISA using ovalbumin for capture and HRPO-coupled, goat anti-murine Ig detecting antibodies with specificity for IgM and IgG subclasses. Each ELISA assay was controlled with sera known to be positive or negative for anti-ovalbumin activity.

The results in FIG. 3G show that old animals provided with DHEA-S only 24 hours prior to immunization with a foreign protein antigen responded even better than normal mature adults in the production of antibody.

This method of reversing age-related decline in humoral responses has been evaluated twice using BALB/c mice and once with C3H/HeN strains of mice. Similar enhancements in antibody production were achieved in all groups of DHEA-S treated, aged groups of mice.

The results described in application U.S. Ser. No. 07/779, 499 and discussed above demonstrate that some of the age-associated changes in immune function are extrinsic in cause, and are mediated by the loss in endogenous production of an essential regulatory steroid prohormone.

EXAMPLE 4

Topical Application of DHEA to Aged Animals Facilitates Changes in the Draining Lymph Node Microenvironment that are Conducive to Successful Immunization Groups of 5 mature adult (13 weeks) and 10 aged BALB/c mice (114 weeks) were used in the study. All of the aged BALB/c mice received a topical application of 10 μg DHEA in 3.5 μl 95% ethanol to the right hind footpad, 3 hours prior to immunization with 100 μg ovalbumin in a 25 μl volume of Maalox. Five of the aged mice were immunized in the right hind footpad (at a site identical to the steroid application), and the other 5 immunized in the left hind footpad (site opposite to the steroid application). Sera from individual mice were collected on Days 0, 3, 5, 7, 10 and 14 following primary immunization. The titre of anti-ovalbumin antibody was assessed by ELISA using ovalbumin for capture and HRPO-coupled, goat anti-murine Ig detecting antibodies with specificity for IgM and IgG subclasses. Bach ELISA assay was controlled with sera known to be positive or negative for anti-ovalbumin activity.

Figure 4:
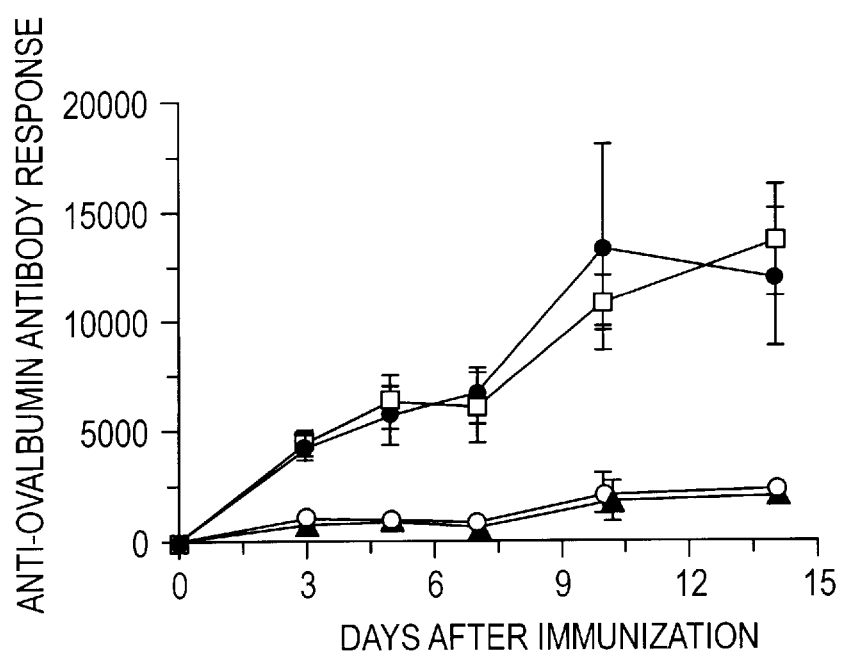
FIG. 4 is a graph showing the effect of topical DHEA application to aged mice on the production of anti-ovalbumin antibodies by the treated mice. The antibody production is shown for mature adult mice (□), aged mice (○), aged mice with DHEA administration at the same site as the antigen (●), and aged mice with DHEA administration at the opposite site of the antigen (▲).
Figure 5A:
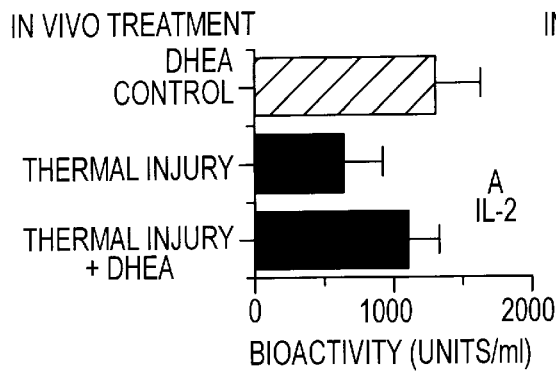
FIG. 5A is a graph showing the effect of DHEA treatment in vivo on the production of IL-2 by activated splenocytes from thermally injured and control mice.
Figure 5B:
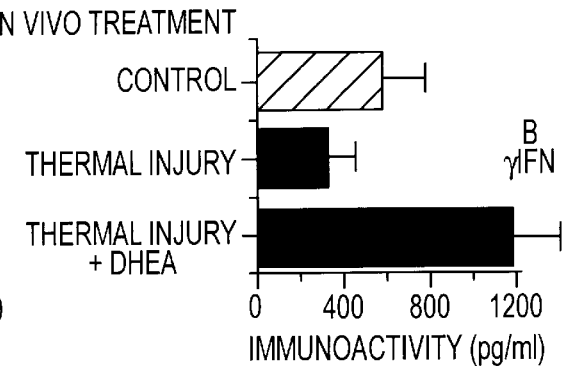
FIG. 5B is a graph showing the effect of DHEA treatment in vivo on the production of γIFN by activated splenocytes from thermally injured and control mice.
Figure 5C:
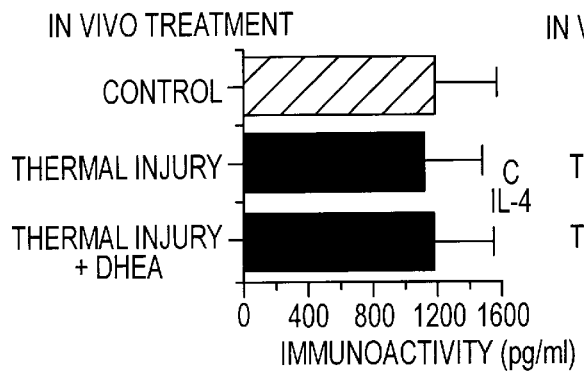
FIG. 5C is a graph showing the effect of DHEA treatment in vivo on the production of IL-4 by activated splenocytes from thermally injured and control mice.
Figure 5D:
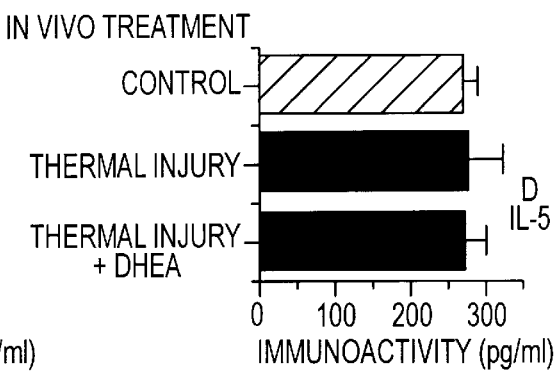
FIG. 5D is a graph showing the effect of DHEA treatment in vivo on the production of IL-5 by activated splenocytes from thermally injured and control mice.
Figure 5E:
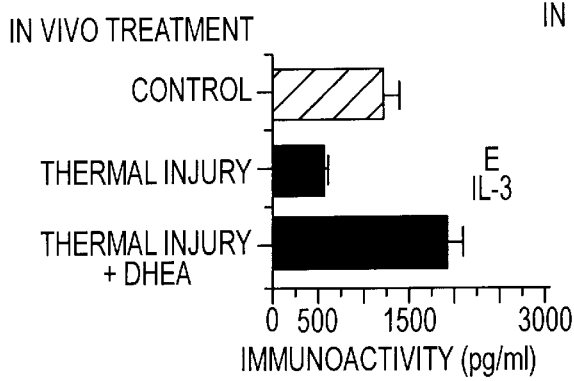
FIG. 5E is a graph showing the effect of DHEA treatment in vivo on the production of IL-3 by activated splenocytes from thermally injured and control mice.
Figure 5F:
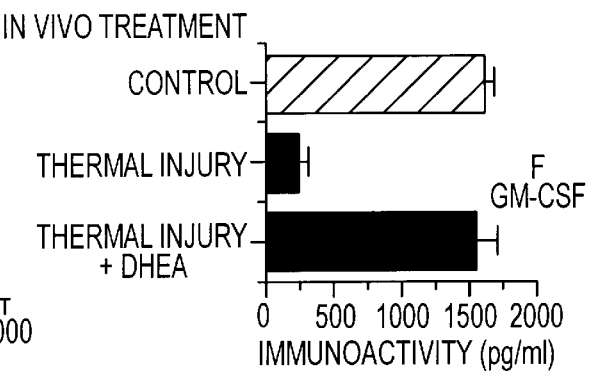
FIG. 5F is a graph showing the effect of DHEA treatment in vivo on the production of CM-CSF by activated splenocytes from thermally injured and control mice.

The results, shown in FIG. 4, establish that a topical application of DHEA, prior to immunization through the same skin site, provided the aged animals with the ability to generate completely normal humoral immune responses. The untreated group of aged animals, and aged animals provided with topical DHEA on the footpads opposite the site of immunization, responded quite poorly to immunization, with minimal antibody being observed.

The results of reversing the age-related decline in humoral responses has been repeated with BALB/c mice, and with C3H/HeN strain of mice. The results establish that the pronounced lymphoid organ-specific changes in the types of lymphokines produced by T cells from aged animals given topical DHEA, can be paralleled by an equally dramatic enhancement in ability to generate potent humoral immune responses to challenge with a foreign antigen protein.

EXAMPLE 5

Treatment in vivo of Thermally-Injured Mice with DUEA Preserves Normal Immune Function Application U.S. Ser. No. 07/779,499 demonstrates that thermal injury to mice caused a depression in the capacity of activated T-cells to secrete IL-2, IFN-γ, IL-3 and GM-CSF, and that this depression could be prevented with DHEA treatment. The following study illustrates that direct administration of DHEA to mice shortly after thermal injury influences their levels of immunocompetence.

Groups of 12 thermally-injured and 6 control BALB/c mice were established as described above. After subjecting the mice to a 20% total body surface area (TBSA) scald burn, six of the thermally-injured mice were given a subcutaneous injection of 100 μg DHEA in a propylene glycol carrier. All remaining animals received the carrier alone. Five days later, all surviving mice were sacrificed and their splenocytes were individually prepared for culture, and activated with anti-$CD_3\epsilon$ to induce lymphokine secretion. Culture supernatants were collected 24 hours after activation and evaluated for lymphokine content, as described in application U.S. Ser. No. 07/779,499. The results of the study are presented in FIGS. 5A–5F, where the bars represent mean±SD for each value. As seen in FIG. 5, DHEA directly influences IL-2, γ-IFN, IL-3, and GM-CSF production by T cells isolated from thermally-injured mice. The administration of a single bolus injection of DHEA (100 μg) 1 hour after thermal injury was sufficient to preserve for at least 5 days a normal capacity by their lymphocytes to produce IL-2, γ-IFN, IL-3, and GM-CSF following activation. No significant changes from normal were observed in the levels of IL-4 and IL-5 made by activated lymphoid cells from these animals.

Figure 6:
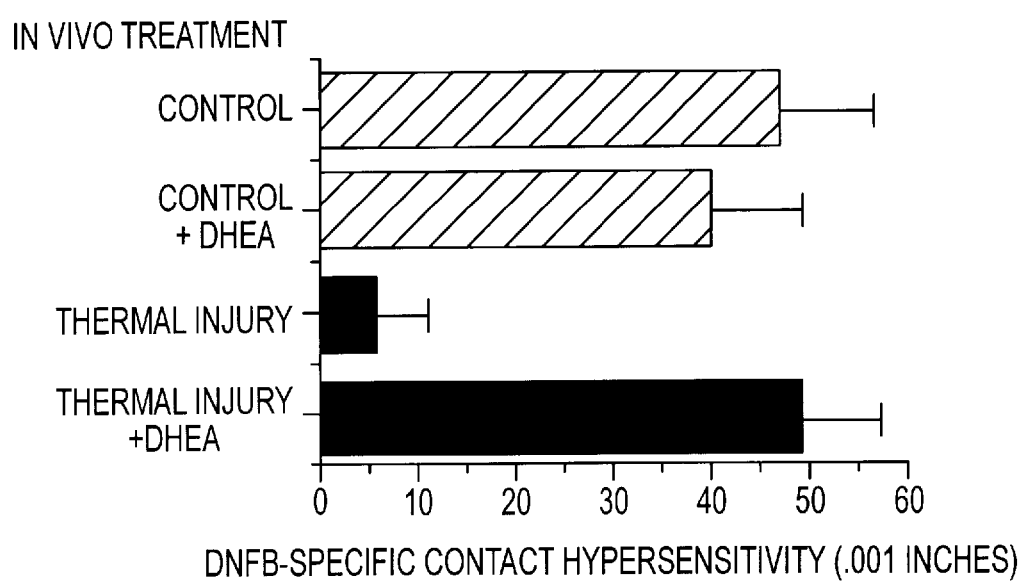
FIG. 6 is a graph showing the effect of DHEA treatment in vivo on contact hypersensitivity responses of thermally injured and control mice.

The effect of DHEA treatment in vivo on the animals' development of cellular immune responses was examined. Parallel groups of thermally-injured and control mice were given either 100 μg DHEA in propylene glycol carrier or the carrier alone 1 hour post-burn. These animals were contact-sensitized 5 days later by administration of DNFB on the abdomen. Challenge doses of DNFB to the right footpads were applied 4 days later. The differences in thickness between the right (challenged) and the left (unchallenged) footpads were used to quantitate the contact hypersensitivity responses. The results are shown in FIG. 6; the bars represent mean±SD for each group of mice. As shown in FIG. 6, the intensity of contact hypersensitivity responses elicited by thermally-injured mice is markedly depressed, as compared to controls. Administration of DHEA to thermally-injured mice was found to completely preserve the ability of these animals to develop contact hypersensitivity responses of normal intensity.

These studies demonstrate that DHEA treatment post-burn is an effective therapy for preserving the capacity of T-lymphocytes from thermally-injured animals to produce normal quantities of a number of lymphokines, especially those that are essential for development of cellular immune responses. This finding is supported by the demonstration in application U.S. Ser. No. 07/779,499 that DHEA-treated thermally-injured mice also retain their capacity to develop normal contact hypersensitivity responses.

EXAMPLE 6

DHEA Treatment in vivo Promotes Resistance to Infection by E. monocytogenes in Thermally-Injured Mice This study addresses the utility of DHEA therapy post-burn in preserving resistance to a bacterial infection. C3H/HeN strain mice are inherently resistant to infection by the gram-positive intracellular pathogen, L. monocylogenes. However, thermal injury results in increased susceptibility to this pathogen. Therefore, a switch from "resistant" to a more "susceptible" phenotype provides a model system to evaluate the effect of DHEA on preserving the "resistant" phenotype in thermally-injured animals.

Figure 7:
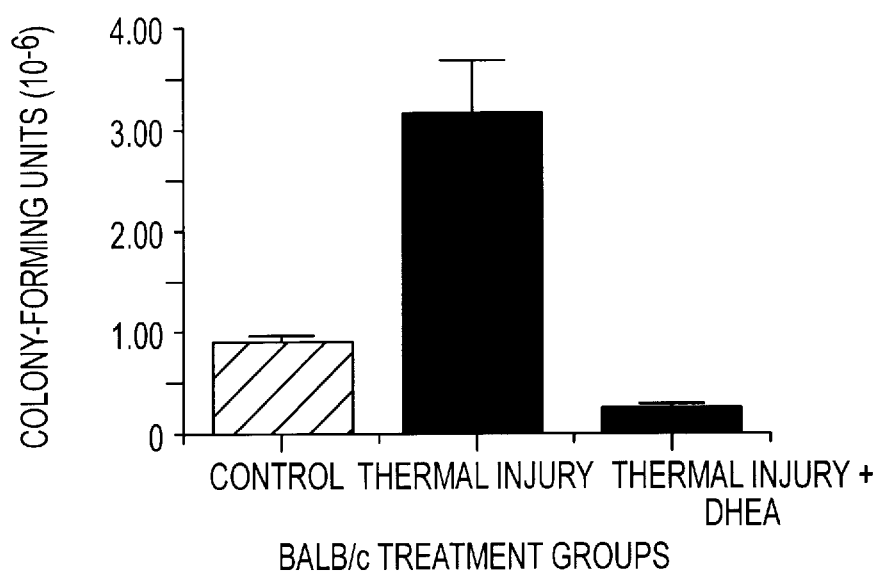
FIG. 7 is a graph showing the effect of DHEA treatment on resistance to *L. monocytogenes* in control and thermally injured C3H mice.

Normal (control) and thermally-injured mice were prepared as described above. Half of the thermally-injured mice received a single bolus injection of 100 µg DHEA subcutaneously within 1 hour after thermal injury. Three days later, all mice were infected with $2 \times 10^6$ viable *L. monocytogenes* organisms, and 3 days after infection the mice were sacrificed and homogenates of individual spleens were prepared. The number of colonies of *L. monocytogenes* per spleen were evaluated using standard methodology, and scored. The results are presented graphically in FIG. 7, where the bars represent means±SEM for each treatment group. The results indicate that thermal injury enhances the susceptibility of the C3H strain mice to infection by *L. monocytogenes*. Of consequence, DHEA treatment of burned animals not only preserves the resistant phenotype, but surprisingly, the level of resistance to infection is actually enhanced by DHEA treatment over that observed in the control group.

EXAMPLE 7

Figure 8:
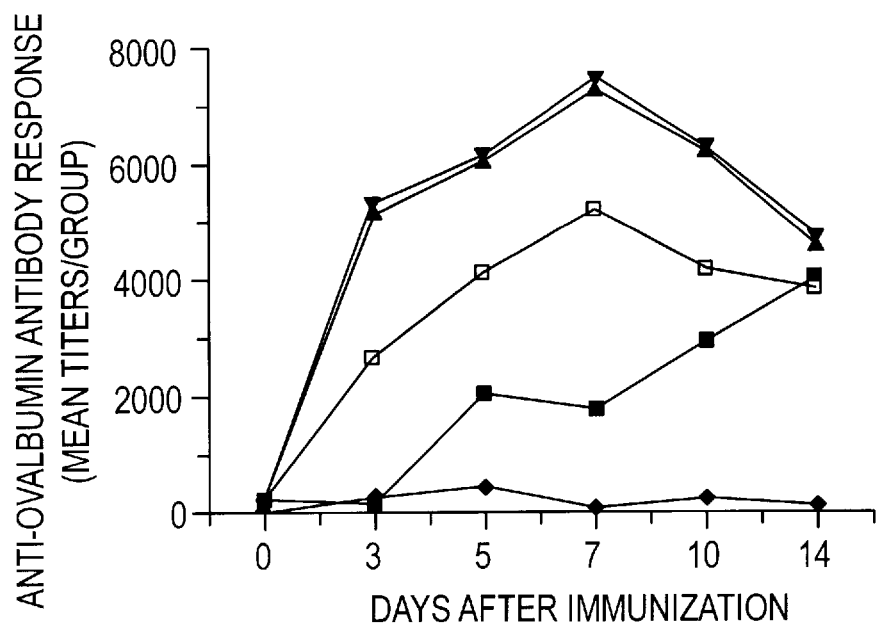
FIG. 8 is a graph showing the effect of topically applied DHEA, 16α-bromo-DHEA and 16α-chloro-DHEA on the anti-ovalbumin antibody response in aged mice. The antibody response is shown for young mice (□), old mice (♦), old mice with DHEA (●), old mice with 16(α-bromo-DHEA (▲), and old mice with 16α-chloro-DHEA (■).

The Effect of 16α-bromo-DHEA and 16α-chloro-DHEA on the Depressed Humoral Responses of Aged Mice to Protein Antigens The effectiveness of the congeners of DHEA, 16α-bromo-DHEA and 16α-chloro-DHEA on age-associated changes in the humoral immune response is demonstrated in the following study. Groups of mature (young) and aged (old) mice were treated by topical administration of 10 µg of DHEA, 16α-bromo-DHEA, or 16α-chloro-DHEA. Three hours subsequent to treatment, the treated and control animals were subjected to an ovalbumin (OVA) challenge as described in the Examples above, and the anti-ovalbumin antibody response was measured at Days 0, 3, 5, 7, 10, and 14 after immunization. The results, shown in FIG. 8, indicate that 16α-bromo-DHEA is as effective as DHEA in restoring humoral immune responsiveness. The 16α-chloro-DHEA yielded a lower, but significant, effect on antibody production.

EXAMPLE 8

Topical Administration of DHEA Enhances Antibody

Production with Vaccines to Hepatitis B Surface Antigen

Figure 9:
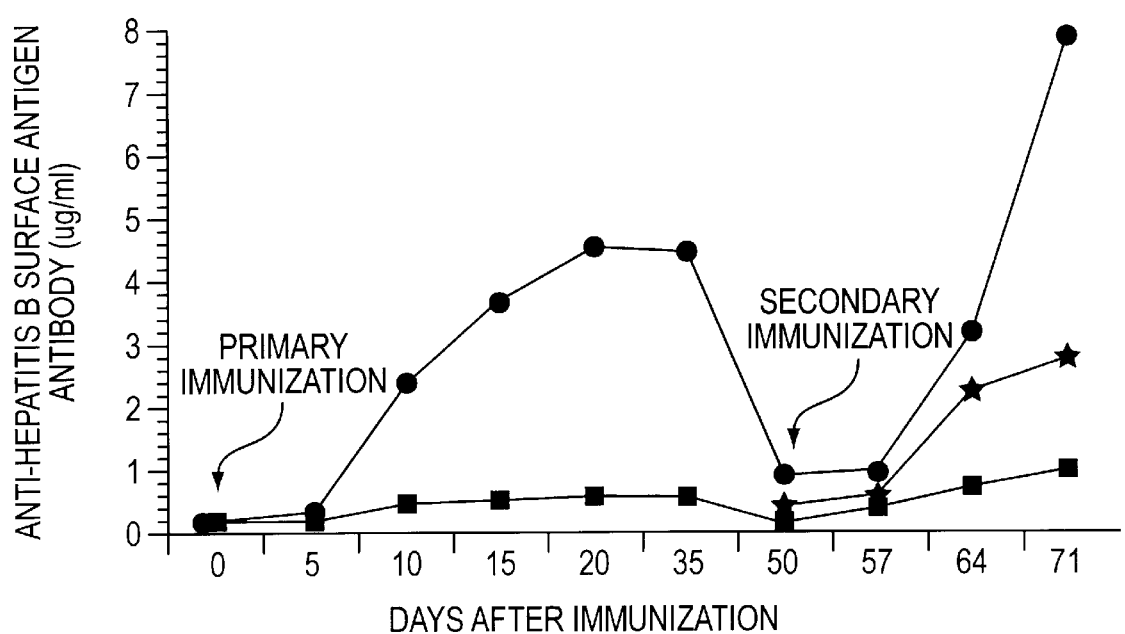
FIG. 9 shows the effect of topical administration of DHEA on vaccination of aged mice with recombinant Hepatitis B Surface Antigen (rHBSAg). The primary and secondary antibody responses are shown for aged mice without DHEA treatment (■), aged mice with DHEA treatment at time of primary immunization (●), and aged mice with DHEA treatment at time of secondary immunization (★).

Groups of five mice [(C3H/HeN×C57BL/6)F1], 72 weeks of age, were immunized with 1.5 µg Hepatitis B surface antigen (HBSAg) in aluminum hydroxide (273 µg/ml; alum). Five of the mice were pre-treated with 10 mg DHEA by topical administration 3 hours prior to immunization. Sera from individual mice were collected during the primary response. Prior to a secondary immunization on Day 50, five of the aged control mice were treated with 10 µg DHEA by topical administration. All of the mice were then given a secondary immunization of 1.5 µg HBSAg in alum and sera were collected weekly. Specific response to the vaccination was measured by quantitative ELISA. Purified rHBSAg diluted in 0.5M Tris-HCl, pH 9.6, at a concentration of 2 µg/ml was dispensed into 96-well plates. Following incubation for a minimum of two hours at room temperature, or overnight at 4° C., all plates were blocked with PBS-0.05% Tween 20/1.0% bovine serum albumin (BSA) for an additional two-hour incubation at room temperature. Prior to adding the test samples, the plates were washed free of blocking buffer using three washes of distilled water and one wash with PBS/0.05% Tween 20. Individual samples were first diluted in PBS 0.05% Tween 20/1.0% BSA, and 100 µl was then dispensed into appropriate wells of the antigen-coated plates. Included on each plate was an Ig standard: a series of two-fold dilutions of either purified IgG (all subclasses) or IgA (reference standards). The reference Ig were captured by goat anti-murine Ig which is known to bind all murine Ig isotypes. These plates were incubated at room temperature overnight, followed by 3× wash in distilled water and one wash in PBS/0.05% Tween 20. The detection antibody (HRP-lined goat anti-mouse Ig specific for IgG and IgA) was diluted in PBS/Tween/10% normal goat serum at a dilution recommended by the manufacturer. After a final incubation and wash series, the ELISA was developed using ABTS-substrate. O.D. readings were recorded at 405 nM using a Vmax 96-well microtest plate spectrophotometer (Molecular Devices, Menlo Park, Calif.). A simple linear regression analysis of the Ig titration generated a reference curve for calculating the amount of specific antibody contained in the test samples. These data are reported as ng/ml±SEM. The results are shown in FIG. 9, and confirm the findings shown in Examples 2 and 3. FIG. 9 demonstrates that topical administration of DHEA provides an enhancement in the immune response for vaccination with HBSAg, as seen by serum anti-HBSAg antibodies.

Similar effects were seen with the topical administration of 1 6α-Br-DHEA.

EXAMPLE 9

Figure 10A:
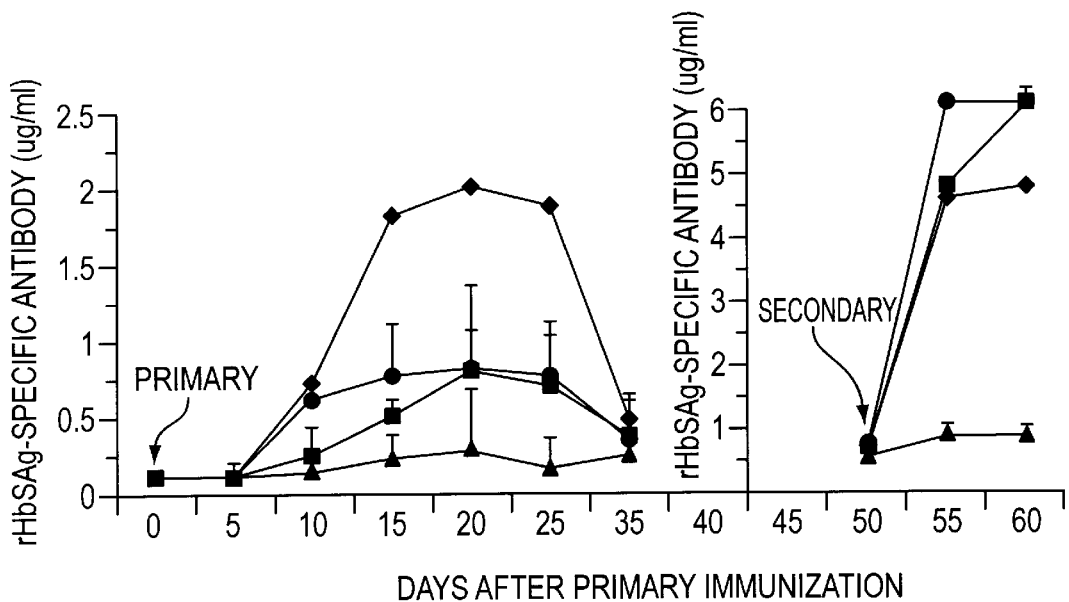
FIG. 10A shows that primary and secondary antibody responses in aged mice following vaccination with rHBSAg is enhanced by topically applied DHEA. The antibody responses are shown for mature mice without DHEA treatment (■), mature mice with DHEA treatment (●), aged mice without DHEA treatment (▲), and aged mice with DHEA treatment (♦).
Figure 10B:
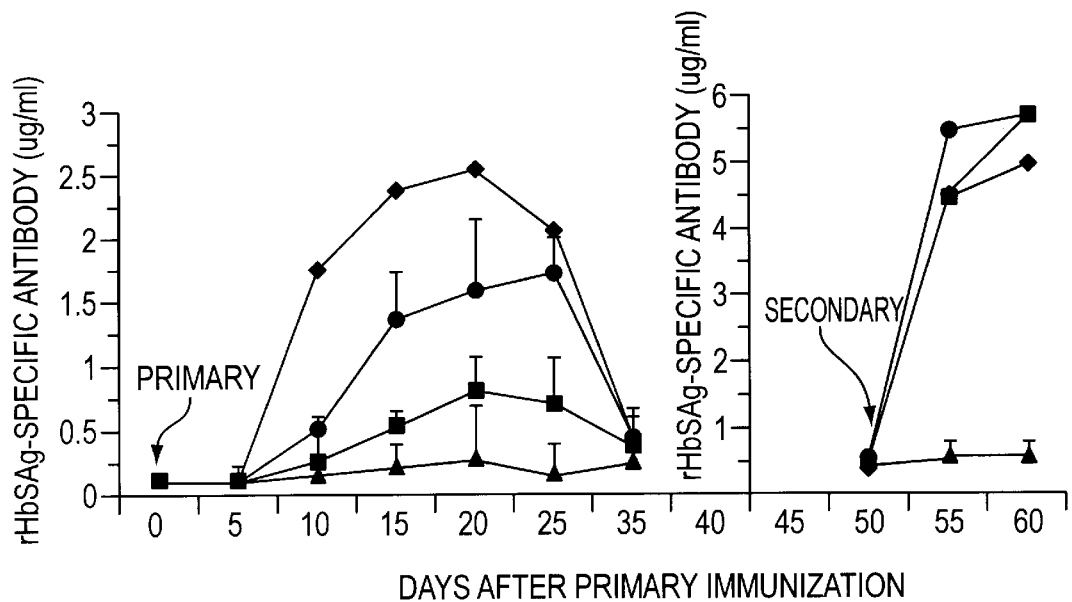
FIG. 10B shows that primary and secondary antibody responses in aged mice following vaccination with rHBSAg is enhanced by incorporating DHEA as a component of the vaccine. The antibody responses are shown for mature mice without DHEA treatment (■), mature mice with DHEA treatment (●), aged mice without DHEA treatment (▲), and aged mice with DHEA treatment (♦).

Administration of DHEA Topically Prior to Vaccination or as a Component of the Vaccine Enhances Antibody Production Aged mice [(C3H×BL/6)F1], approximately 24 months old, were given a topical application of 10 µg DHEA three hours prior to vaccination with a recombinant Hepatitis B surface antigen (rHBSAg). Alternatively, 10 µg DHEA was incorporated into the vaccine/alum mixture prior to immunization. Untreated aged mice, and untreated mature adult mice [C3H×BL/6)F1], 26 weeks of age, were administered the ethanol vehicle without DHEA. All of the test mice were vaccinated with rHbSAg (1.0 µg) in 25 µl alum (273 µg/ml) through the anatomic site of DHEA or ethanol application. Serum samples were collected from individual mice at multiple times during the primary response. A secondary antigen exposure was given to all mice 50 days after the primary immunization. Recall responses were stimulated without any additional treatment with DHEA. Serum samples were then collected 5 and 10 days following secondary antigen exposure. Individual serum samples were evaluated by quantitative ELISA as described above to determine the amount of HBSAg-specific antibody. The mean and SEM antibody responses at each interval are shown in FIGS. 10A and 10B. The results show that the serum antibody response to rHBSAg was enhanced in aged mice when the mice were treated prior to vaccination with topical DHEA (FIG. 10A) or were treated with DHEA incorporated in the vaccine (FIG. 10B).

EXAMPLE 10

Figure 11:
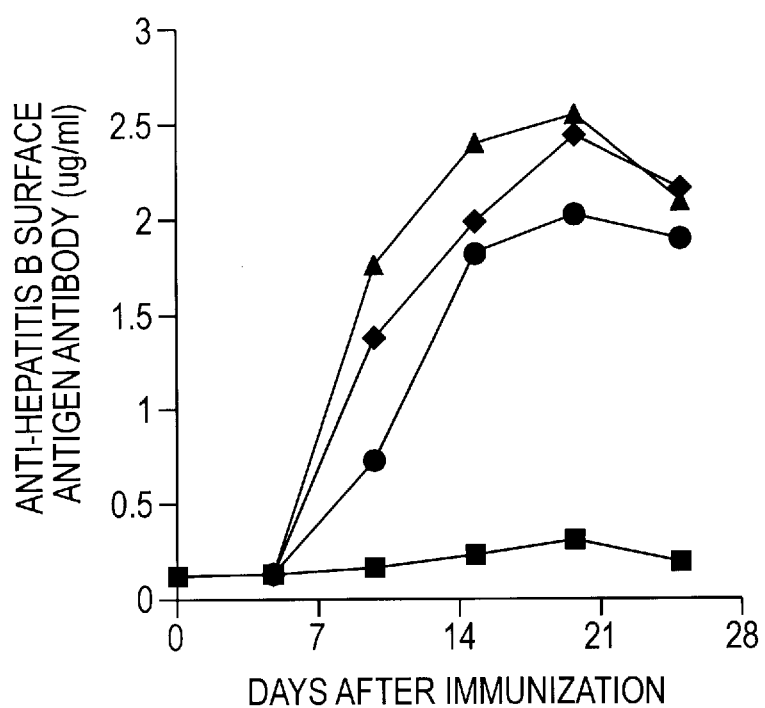
FIG. 11 shows that the antibody response in aged mice, following vaccination with rHBSAg, is enhanced by treatment with DHEA or DHEA-S. The antibody responses are shown for aged mice without treatment (■), aged mice with topical DHEA treatment (●), aged mice with DHEA incorporated in the vaccine (▲), and aged mice with DHEA-S incorporated in the vaccine (♦).

Administration of DHEA or DHEA-S Topically or as a Component of the Vaccine Enhanced Antibody Production Groups of sex- and age-matched mice [(C3H×C57 BL/6) F1], greater than 24 months of age, were immunized subcutaneously with rHBSAg (1.0 μg in 25 μl alum (273 μg/ml)). Animals were given a topical administration of 10 μg DHEA three hours prior to vaccination. Alternatively, 10 μg DHEA or DHEA-S was incorporated into the vaccine/alum mixture prior to immunization. Untreated aged mice were administered the ethanol vehicle without DHEA. Serum samples were collected from individual mice at multiple times and were evaluated by quantitative ELISA as described above, to determine the amount of HbSAg-specific antibody. The mean antibody response is shown in FIG. 11. The results show that the serum antibody response was enhanced in aged mice when the mice were treated prior to vaccination with topical DHEA (●) or were treated with DHEA (▲) or DHEA-S (♦) incorporated in the vaccine.

Similar results are obtained when DHEA congeners of formula I as set forth in Table A are used in place of DHEA or DHEA-S.

TABLE A

DHEA Congeners Useful for Vaccine Enhanced Antibody Production

| $R^1$ | $R^2$ | $R^3$ | X |
|---|---|---|---|
| O | O | H | H |
| $OOCC_2H_5$ | O | H | Br |
| $OCH_5$ | O | H | H |
| SH | O | H | H |
| $SOC(CH_2)_5CH_3$ | O | H | H |
| $SCH_3$ | O | H | H |
| O | O | OH | H |
| OH | O | O | Br |
| OH | O | $OOC(CH_2)_2C_6H_5$ | H |
| OH | O | $OOCC_2H_5$ | H |
| OH | O | OH | H |
| SH | O | SH | H |
| $SCH_3$ | O | SH | H |
| OH | OH | H | H |
| O | OH | H | Br |
| OH | $OOCC_2H_5$ | H | H |
| OH | $OC_2H_4$ | H | H |
| SH | OH | H | H |
| $SCH_3$ | OH | H | H |
| O | OH | O | H |
| OH | OH | O | Br |
| cypionate | $OOCH_3$ | O | H |
| OH | OH | OH | H |
| SH | OH | SH | H |
| SH | OH | $SCH_3$ | H |
| OH | SH | H | H |
| OH | SH | H | Br |
| $OOC(CH_2)_2CO_2H$ | SH | H | H |
| SH | SH | H | H |
| SH | $SC_2H_4$ | H | H |
| O | SH | OH | H |
| $OC_2H_5$ | SH | OH | H |
| $SOCCH_3$ | SH | SH | H |
| glucuronate | O | O | H |
| $OSO_2OH$ | O | OH | H |
| OH | $OSO_2OH$ | OH | H |
| $OSO_2OCC_4H_9$ | O | OH | H |
| $OP(O)(OH)OCCH_3$ | O | O | H |

EXAMPLE 11

Administration of DHEA Enhances Immunization with Suboptimal Doses of rHBSAg

Figure 12A:
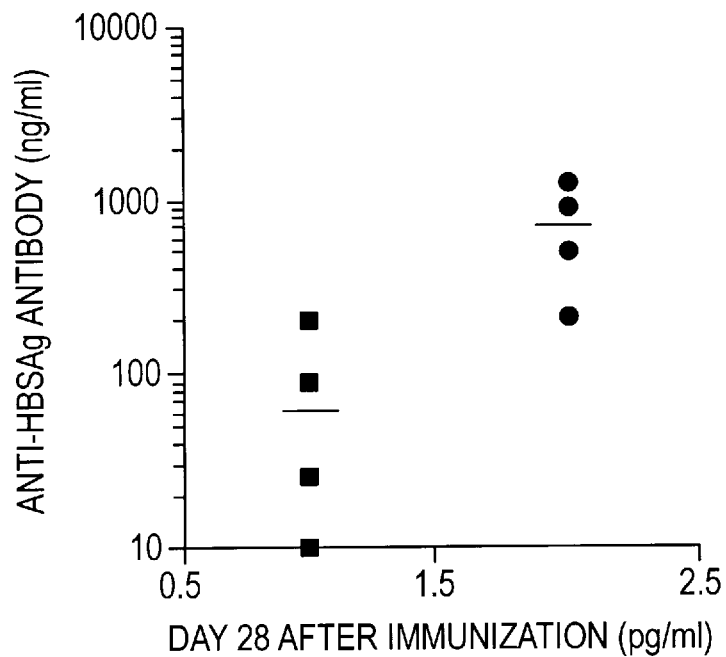
FIG. 12A shows that DHEA administration enhances the efficiency of immunization with suboptimal doses of rHBSAg. The antibody responses are shown for mice without DHEA treatment (■) and with DHEA treatment (●), for vaccination with 0.5 $\mu$g rHBSAg/mouse.
Figure 12B:
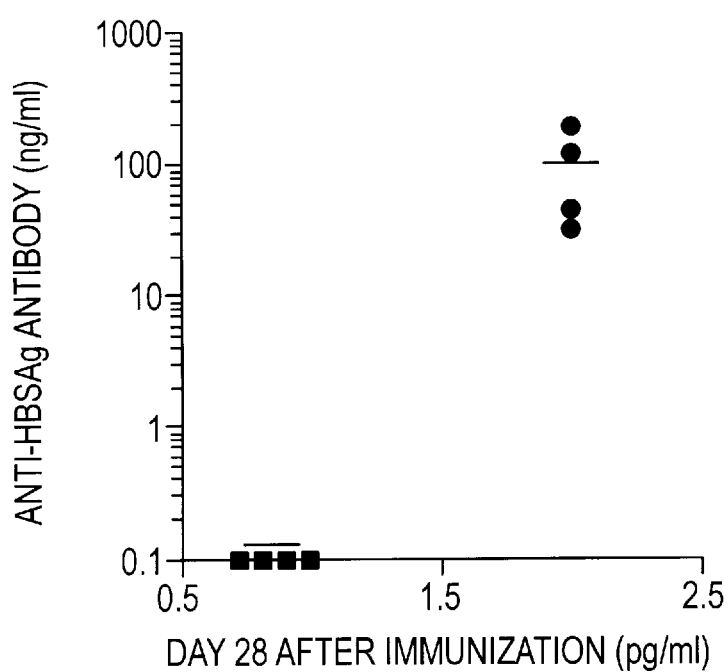
FIG. 12B shows that DHEA administration enhances the efficiency of immunization with suboptimal doses of rHBSAg. The antibody responses are shown for mice without DHEA treatment (■) and with DHEA treatment (●), for vaccination with 0.1 $\mu$g rHB SAg/mouse.
Figures 13A, 13B:
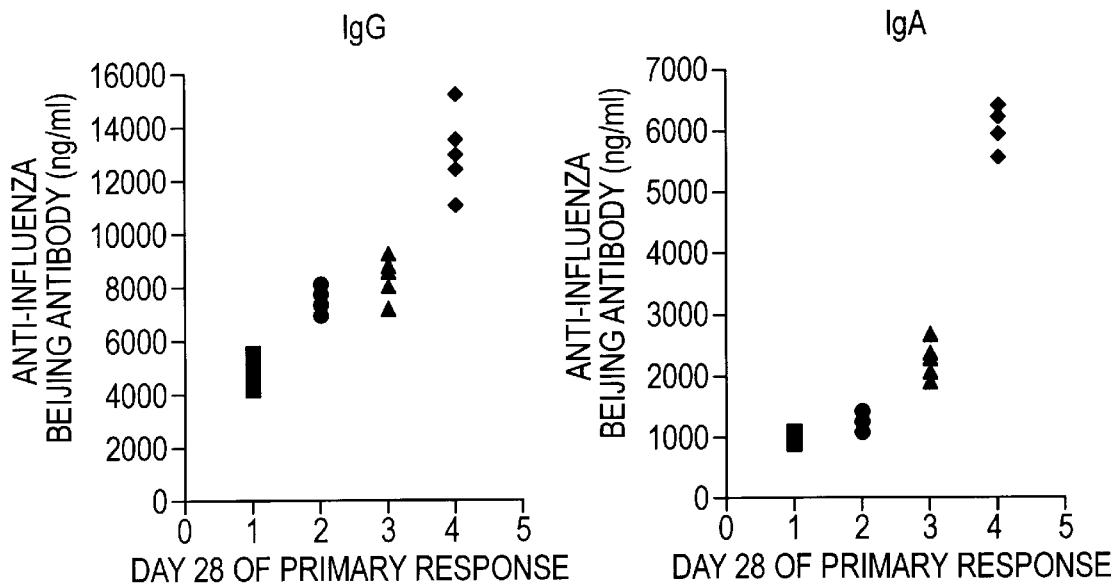
FIGS. 13A and 13B show that serum (systemic) antibody response in mature mice following vaccination with Influenza-A Beijing strain is synergistically enhanced by treatment with DHEA and 1,25(OH)$_2$D$_3$. Antibody responses at Day 28 are shown for mice without treatment (■), mice treated with 2 $\mu$g DHEA in vaccine (●), mice treated with 0.1 $\mu$g 1,25(OH)$_2$D$_3$ in vaccine (▲), and mice treated with 2 $\mu$g DHEA and 0.1 $\mu$g 1,25(OH)$_2$D$_3$ in vaccine (♦).
Figures 13C, 13D:
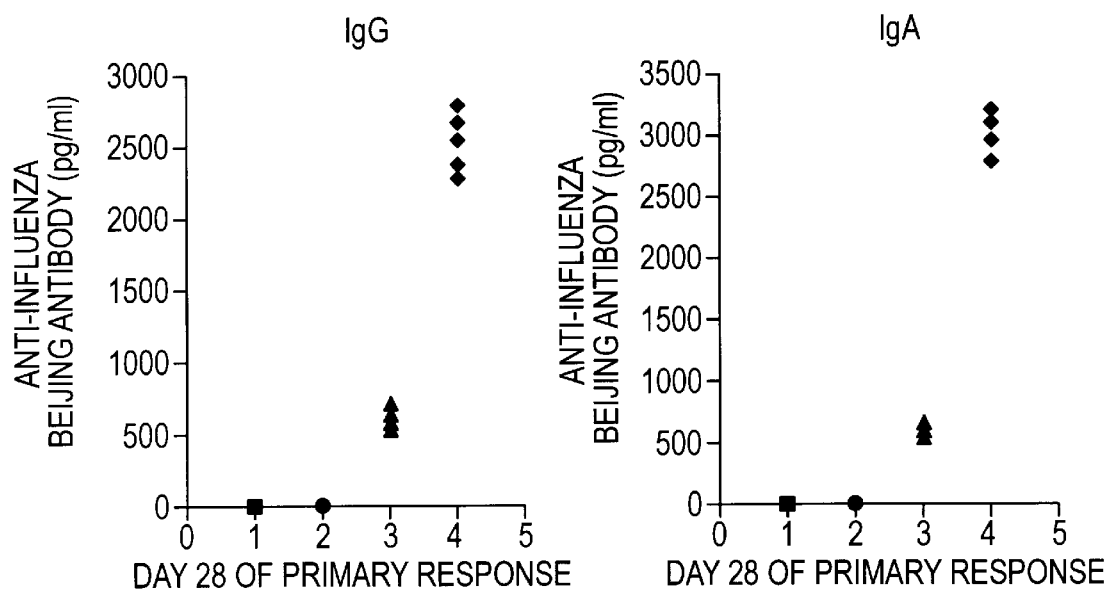
FIGS. 13C and 13D show that mucosal antibody response in mature mice following vaccination with Influenza-A Beijing strain is synergistically enhanced by treatment with DHEA and 1,25(OH)$_2$D$_3$. Antibody responses at Day 28 are shown for mice without treatment (■), mice treated with 2 $\mu$g DHEA in vaccine (●), mice treated with 0.1 $\mu$g 1,25(OH)$_2$D$_3$ in vaccine (▲), and mice treated with 2 $\mu$g DHEA and 0.1 $\mu$g 1,25(OH)$_2$D$_3$ in vaccine (■).
Figure 14A:
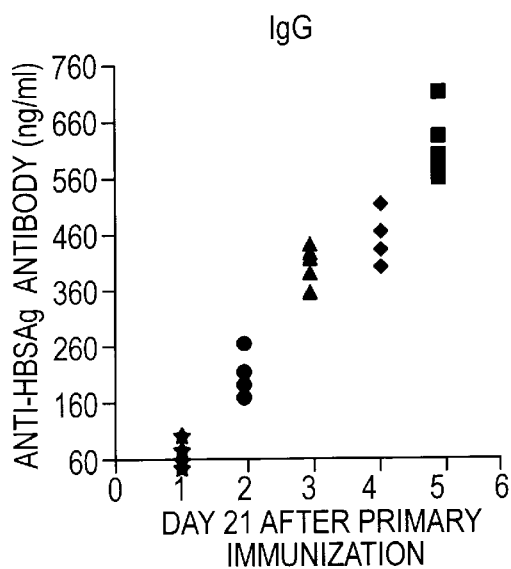
FIGS. 14A and 14B show that serum (systemic) antibody response in mature mice following vaccination with rHBSAg is synergistically enhanced by treatment with DHEA and 1,25(OH)$_2$D$_3$. Antibody responses at Day 21 are shown for non-immunized mice (★), mice without treatment (●), mice treated with 2 $\mu$g DHEA in vaccine (♦), mice treated with 0.1 $\mu$g 1,25(OH)$_2$D$_3$ in vaccine (▲), and mice treated with 2 $\mu$g DHEA and 0.1 $\mu$g 1,25(OH)$_2$D$_3$ in vaccine (■).
Figure 14B:
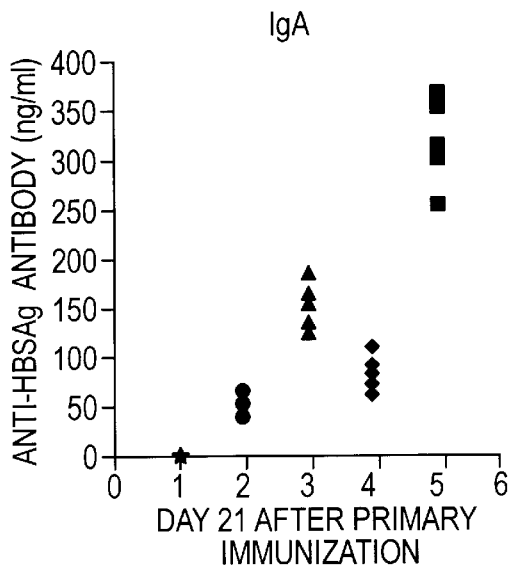
Figure 14C:
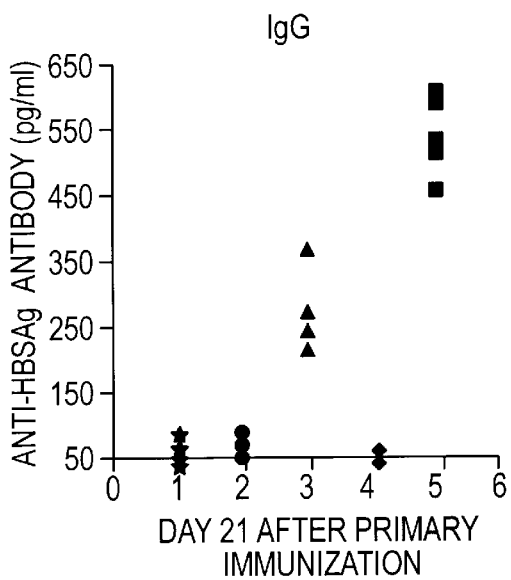
FIGS. 14C and 14D show that mucosal antibody response in mature mice following vaccination with rHBSAg is synergistically enhanced by treatment with DHEA and 1,25 (OH)$_2$D$_3$. Antibody responses at Day 21 are shown for non-immunized mice (★), mice without treatment (●), mice treated with 2 $\mu$g DHEA in vaccine (♦), mice treated with 0.1 $\mu$g 1,25(OH)$_2$D$_3$ in vaccine (▲), and mice treated with 2 $\mu$g DHEA and 0.1 $\mu$g 1,25(OH)$_2$D$_3$ in vaccine (■).
Figure 14D:
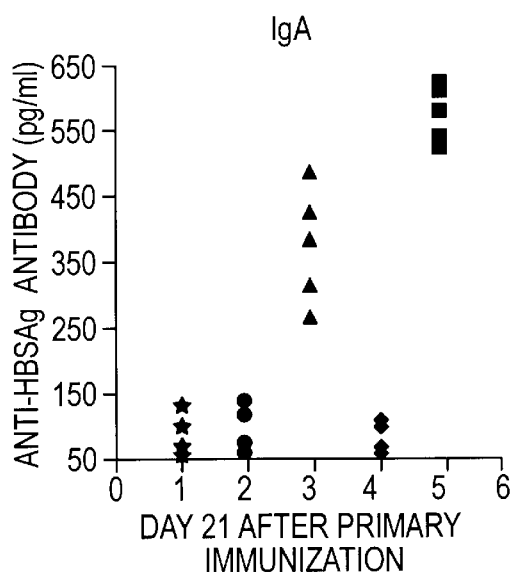
Figure 15A:
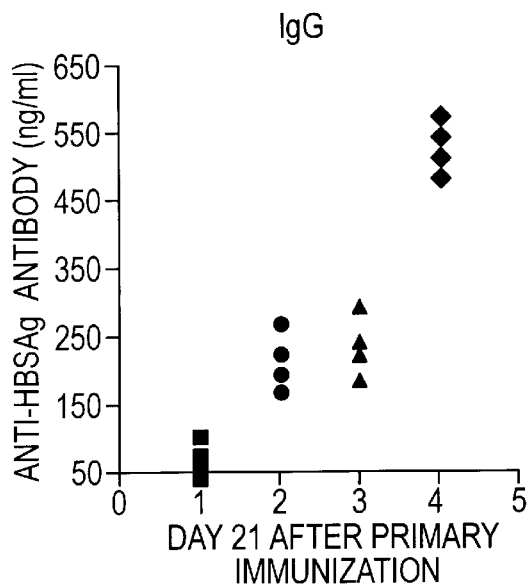
FIGS. 15A and 15B show that serum (systemic) antibody response in mature mice following vaccination with rHBSAg is synergistically enhanced by treatment with DHEA and all trans-retinoic acid. Antibody responses at Day 21 are shown for non-immunized mice (■), mice without treatment (●), mice treated with 5.0 $\mu$g all trans-retinoic acid in vaccine (▲), and mice treated with 2 $\mu$g DHEA and 5.0 $\mu$g all trans-retinoic acid in vaccine (♦).
Figure 15B:
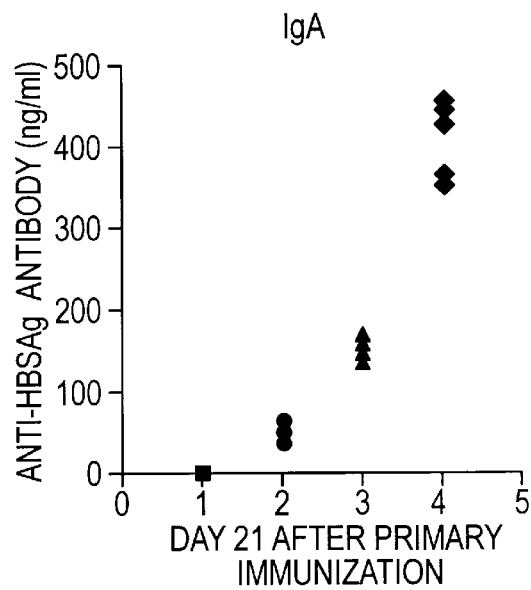
Figure 15C:
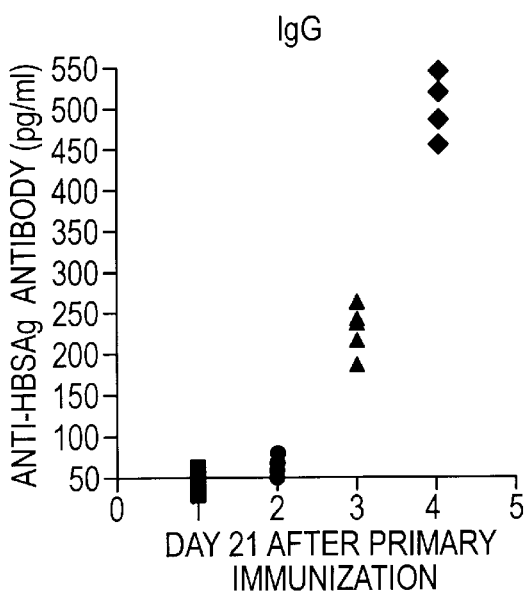
FIGS. 15C and 15D show that mucosal antibody response in mature mice following vaccination with rHBSAg is synergistically enhanced by treatment with DHEA and all trans-retinoic acid. Antibody responses at Day 21 are shown for non-immunized mice (■), mice without treatment (●), mice treated with 5.0 $\mu$g all trans-retinoic acid in vaccine (▲), and mice treated with 2 $\mu$g DHEA and 5.0 $\mu$g all trans-retinoic acid in vaccine (♦).
Figure 15D:
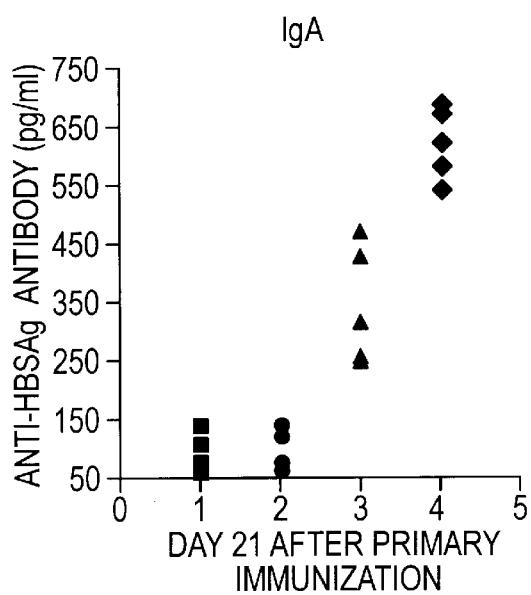

Groups of 8 mature adult CF-1 mice were immunized with either 0.5 μg or 0.1 μg rHBSAg in 25 μl alum (273 μg/ml), subcutaneously in a single hind footpad. Four mice in each group were pre-treated with either 10 μg DHEA in ethanol or the ethanol vehicle alone, topically applied to the same site as the immunization. Serum samples from individual mice were collected and analyzed for specific antibody, as described above. The scattergram shows the responses in ng/ml of each mouse to the vaccine at 28 days post-immunization. FIG. 12 shows that the antibody response to rHBSAg was enhanced for the suboptimal doses of 0.5 μg rHBSAg (FIG. 12A) and of 0.1 μg rHBSAg (FIG. 12B). Thus, DHEA enhances the efficiency of vaccination in normal immunocompetent mice, when the dose of antigen has been previously established to be suboptimal.

EXAMPLE 12

Topical Administration of DHEA Enhances Serum Antibody Production in Elderly Mice Upon Vaccination Examples 2 and 3 show that DHEA-S administration restored the ability of aged mice to mount a humoral immune response against ovalbumin. This example demonstrates that topical administration of DHEA prior to vaccination against several different antigens enhances serum antibody production in elderly mice.

Aged mice [C3H/HeN], approximately 22–27 months of age, were given a topical application of 10 μg DHEA three hours prior to vaccination with Diphtheria toxoid (Dt, 1.0 μg), Tetanus toxoid (Tt, 1.0 μg), or a Hemophilus Influenza Type b conjugate vaccine coupled to Dt (500 ng of Hib polysaccharide chemically coupled to 1.25 μg Dt) in standard alum adjuvant. Untreated aged mice and untreated mature adult mice [C3H/HeN], 17–24 weeks of age, were administered the ethanol vehicle without DHEA. Serum samples were collected from individual mice at multiple times during the primary response. Individual serum samples were evaluated by quantitative ELISA as described above, using purified Dt (diluted in 0.05M Tris-HCl (pH 9.6) at a concentration of 2.0 μg/ml), purified Tt (diluted in 0.05M Tris-HCl (pH 9.6) at a concentration of 2 μg/ml), or Hib-meningococcal protein conjugate (diluted in 0.05M Tris-HCl (pH 9.6) at a concentration of 200 ng/ml polysaccharide). The mean primary antibody response at Day 28 is shown in Table 1. The results show that the serum antibody responses to these antigens were enhanced in aged mice with topical administration of DHEA prior to vaccination. Similar results were obtained when DHEA is incorporated in the vaccine.

TABLE 1

Serum Antibody Production

| | Primary Antibody Response (μg/ml) | | |
|---|---|---|---|
| Immunogen | Mature Adult | Aged | DHEA-treated Aged |
| Diphtheria Toxoid (1.0 μg) | 1.65 | 0.43 | 5.75 |
| Tetanus Toxoid (1.0 μg) | 6.8 | 2.3 | 4.6 |
| Hemophilus Influenza Type b Conjugate Vaccine: | | | |
| Hib Polysaccharide (500 ng) | 13.3 | 6.4 | 16.2 |
| Diphtheria Toxoid (1.25 μg) | 5.8 | 3.5 | 7.8 |

EXAMPLE 13

Administration of DHEA-S in Vaccine Enhances Serum Antibody Production in Elderly Mice Examples 2 and 3 showed that DHEA-S administration restored the ability of aged mice to mount a humoral immune response against ovalbumin. Example 12 demonstrated that topical administration of DHEA prior to immunization enhanced the production of serum anti-bodies in elderly mice. This Example demonstrates that administration of DHEA-S in the antigen vehicle also enhances serum antibody production in elderly mice. Aged mice [C3H/HeN], 22–27 months of age, were vaccinated with inactivated Influenza A Beijing strain (0.1 µg) in a standard alum adjuvant (25 µl; 273 µg alum/ml) which also contained 10 µg DHEA-S. Untreated aged mice and untreated mature adult mice [C3 H/HeN], 17–24 weeks of age, were administered the vaccine without DHEA-S. Serum samples were collected from individual mice at multiple times during the primary response. Individual serum samples were evaluated by quantitative ELISA as described above, using purified inactivated Influenza A (diluted in 0.05M Tris-HCl (pH 9.6) at a concentration of 0.1 µg/ml). The mean primary antibody response at Day 28 is shown in Table 2. The results show that the serum antibody response to this antigen was enhanced in aged mice with incorporation of DHEA-S in the vaccine.

Similar results are obtained for the DHEA congeners of Table A when substituted for DHEA-S.

TABLE 2

Serum Antibody Production

| Immunogen | Primary Antibody Response (µg/ml) | | |
|---|---|---|---|
| | Mature Adult | Aged | DHEA-treated Aged |
| Inactivated Influenza A Virus (0.1 µg) | 4.7 | 0.16 | 4.3 |

EXAMPLE 14

Administration of $1,25(OH)_2D_3$ With Vaccination to Diphtheria Toxoid Enhances Antibody Response Groups of 3–5 age-matched C3H/HeN female mice were given primary immunization subcutaneously in the right footpad with 10 µg Diphtheria toxoid (Dt; Connaught Laboratories) in alum (273 µg/ml). One group of mice were administered 2 µg $1,25(OH)_2D_3$ epicutaneously to the right footpad surface on Day 0. A second group of mice was similarly administered $1,25(OH)_2D_3$ on Day 5 after immunization. A third group of mice (control) received an equal volume of the ethanol carrier. After weekly sampling of serum, mice were secondarily immunized subcutaneously through an intrapelvic route with Dt and no additional exposure to $1,25(OH)_2D_3$. Serum samples were collected and all primary and secondary samples were then assayed individually using a Dt-specific, quantitative ELISA for IgG and IgA, using purified Dt diluted in 0.05M Tris-HCl (pH 9.6) at a concentration of 2.0 µg/ml. The purified Dt was dispensed into 96-well plates. Following incubation for a minimum of two hours at room temperature, or overnight at 4° C., all plates were blocked with PBS-0.05% Tween 20/1.0% bovine serum albumin (BSA) for an additional two-hour incubation at room temperature. Prior to adding the test samples, the plates were washed free of blocking buffer using three washes of distilled water and one wash with PBS/0.05% Tween 20. Individual samples were first diluted in PBS 0.05% Tween 20/1.0% BSA and 100 ml was then dispensed into appropriate wells of the antigen-coated plates. Included on each plate was an Ig standard: a series of two-fold dilutions of either purified IgG (all subclasses) or IgA (reference standards). The reference Ig were captured by goat anti-murine Ig which is known to bind all murine Ig isotypes. These plates were incubated at room temperature overnight, followed by 3× wash in distilled water and one wash in PBS/0.05% Tween 20. The detection antibody (HRP-lined goat anti-mouse Ig specific for IgG and IgA) was diluted in PBS/Tween/10% normal goat serum at a dilution recommended by the manufacturer. After a final incubation and wash series, the ELISA was developed using ABTS-substrate. O.D. readings were recorded at 405 nM using a Vmax 96-well microtest plate spectrophotometer (Molecular Devices, Menlo Park, Calif.). A simple linear regression analysis of the Ig titration generated a reference curve for calculating the amount of specific antibody contained in the test samples. These data are reported as ng/ml±SEM. It was found that mice which received $1,25(OH)_2D_3$ at Day 0 showed a slight enhancement in serum levels of IgG. Mice which received $1,25(OH)_2D_3$ at Day 0 or Day 5 showed a substantial enhancement in serum levels of IgA. Substantial enhancements in serum IgG and IgA were seen when mice were immunized with Hemophilus Influenza type b polysaccharide conjugate vaccine, Hib coupled to Dt(HibCV) and received $1,25(OH)_2D_3$ on Day 5. Similar results were obtained with topical administration of $1,25(OH)_2D_3$ to other antigens, as shown in the following Example.

EXAMPLE 15

Administration of $1,25(OH)_2D_3$ Enhances Antibody Response to Vaccinations with Various Antigens Sex- and age-matched mice [CF-1] were immunized subcutaneously with the following antigens in alum (273 µg/ml):

Chlamydia trachomatus peptide (5 µg)
Hemophilus Influenza untypeable (1.0 µg)
Hemophilus Influenza Type b conjugate vaccine coupled to Dt (500 ng of Hib polysaccharide chemically coupled to 1.25 µg Dt)
Respiratory syncytial virus peptide (1 µg)
Hepatitis B Surface Antigen (1 µg)
HIV gp 120 (0.5 µg)
Neisseria gonorrhoeae pilin protein (1 µg)
Diphtheria toxoid (1 µg)

One group of mice was administered 2 µg $1,25(OH)_2D_3$ epicutaneously at the same site on Day 0. Untreated mice were administered the ethanol vehicle without $1,25(OH)_2D_3$. Serum samples and mucosal samples (vaginal lavage samples (75 µl of physiological saline)) were collected from individual mice at multiple times during the primary response. Individual serum and mucosal samples were evaluated by quantitative ELISA as described in Example 14, using the appropriate antigens. The mean primary antibody responses at Day 28 are shown in Table 3 for the serum (systemic or humoral) antibodies and in Table 4 for the mucosal antibodies. The results show that the serum and mucosal antibody responses were enhanced in mice with topical administration of $1,25(OH)_2D_3$. Mucosal antibodies (both IgG and IgA) were also detected in other mucosal secretions, including lacrimal, rectal, oral and lung. Similar results were obtained when all trans-retinoic acid is used in place of $1,25(OH)_2D_3$.

TABLE 3

Secretory Antibody Production

| | Systemic Ig (ng/ml) | | | |
|---|---|---|---|---|
| | Vaccine Only | | Vaccine With Topical 1,25(OH)$_2$D$_3$ | |
| | IgG | IgA | IgG | IgA |
| Chlamydia trachomatus peptide (5 µg) | <0.02 | 43 | 55 | 85 |
| Hemophilus influenza untypeable Hemophilus Influenza type b-CV: | 3235 | 69 | 4712 | 93.2 |
| - Hib polysaccharide (500 ng) | 25 | 12.5 | 125 | 76.1 |
| - Diphtheria toxoid (1.25 µg) | 853 | 11.6 | 1285 | 20.3 |
| Respiratory Syncytial virus peptide (1 µg) | 2746 | 225 | 8440 | 754 |
| Hepatitis B surface antigen (1 µg) | 254 | 58 | 902 | 149 |
| HIV gp 120 (.5 µg) | 1356 | 854 | 2459 | 1408 |
| Neisseria gonorrhoeae pilin protein (1 µg) | 844 | 16.3 | 1841 | 29.1 |
| Diphtheria toxoid (1 µg) | 1233 | 23 | 1640 | 137 |

TABLE 4

Secretory Antibody Production

| | Mucosal Ig (pg/ml) | | | |
|---|---|---|---|---|
| | Vaccine Only | | Vaccine With Topical 1,25(OH)$_2$D$_3$ | |
| | IgG | IgA | IgG | IgA |
| Chlamydia trachomatus peptide (5 µg) | <20 | 397 | 759 | 2234 |
| Hemophilus Influenza untypeable Hemophilus Influenza type b-CV: | 719 | 1384 | 2081 | 1865 |
| - Hib polysaccharide (500 ng) | 180 | 440 | 280 | 1720 |
| - Diphtheria toxoid (1.25 µg) | 310 | 400 | 590 | 1400 |
| Respiratory Syncytial virus peptide (1 µg) | <20 | <20 | 1544 | 1264 |
| Hepatitis B surface antigen (1 µg) | <20 | <20 | 450 | 250 |
| HIV gp 120 (.5 µg) | 35 | 45 | 1428 | 755 |
| Neisseria gonorrhoeae pilin protein (1 µg) | 6341 | 1063 | 10235 | 5486 |
| Diphtheria toxoid (1 µg) | <20 | 60 | 1.8 | 1125 |

The above example was repeated, using 0.1 µg 1,25(OH)$_2$D$_3$ in the vaccine (in a total volume of 25 µl with alum (250 µg/ml)) instead of topical administration of the 1,25(OH)$_2$D$_3$. Identical results were obtained as set forth in Tables 3 and 4.

EXAMPLE 16

Comparative Effect of 1,25(OH)$_2$D$_3$ and All Trans-Retinoic Acid on Immunoglobulin Production Groups of sex- and age-matched mice [CF-1], 17–24 weeks of age, were immunized with 1.0 µg HBSAg in 25 µl alum. The mice in each group were immunized with either vaccine alone, vaccine with 0.1 µg 1,25(OH)$_2$D$_3$, or vaccine with 5 µl all trans-retinoic acid. The agents were incorporated directly into the vaccine mixture. Individual serum (systemic) samples and mucosal samples (vaginal lavage samples (75 µl of physiological saline)) were collected at weekly intervals during the primary response. The mean quantities of antibodies (IgG and IgA) detected in the serum and mucosal secretions 28 days after a single immunization are shown in Table 5. The results show that both 1,25(OH)$_2$D$_3$ and all trans-retinoic acid enhance both the serum and mucosal antibody response.

TABLE 5

Antibody Production with 1,25(OH)$_2$D$_3$ or All Trans-Retinoic Acid

| | Systemic Ig (ng/ml) | | Mucosal Ig (ng/ml) | |
|---|---|---|---|---|
| Composition of Vaccine | IgG | IgA | IgG | IgA |
| Vaccine only | 225 | 160 | 35 | <20 |
| Vaccine w/0.1 µg 1,25(OH)$_2$D$_3$ | 457 | 494 | 352 | 341 |
| Vaccine w/5 µg All Trans-Retinoic Acid | 295 | 531 | 437 | 311 |

EXAMPLE 17

Administration of DHEA and 1,25(OH)$_2$D$_3$ in Vaccine Enhances Serum and Mucosal Antibody Response Groups of five mature adult C3H mice were immunized with 0.1 µg inactivated Influenza-A Beijing strain in 25 µl of alum (273 µg/ml) in the hind footpad. The mice in each group were immunized with either vaccine alone, vaccine plus 2 µg DHEA, vaccine plus 0.1 µg 1,25(OH)$_2$D$_3$ or vaccine with both 2 µg DHEA and 0.1 µg 1,25(OH)$_2$D$_3$. The agents were incorporated directly into the vaccine mixture. Individual serum (systemic) samples and mucosal samples (vaginal lavages (75 µl physiological saline)) were collected at weekly intervals during the primary response and evaluated by quantitative ELISA. FIGS. 13A–13D show the mean quantities of antibody detected in serum (A and B) and mucosal secretions (C and D) 28 days after a single immunization, respectively. The results show that co-administration of DHEA and 1,25(OH)$_2$D$_3$ in the vaccine synergistically enhances both the serum and mucosal antibody response.

EXAMPLE 18

Administration of DHEA and 1,25(OH)$_2$D$_3$ in Vaccine Enhances Serum and Mucosal Antibody Response Groups of five mature adult CF1 mice were immunized with 1.0 µg rHBSAg in 25 µl of alum (273 µg/ml) in the hind footpad. The mice in each group were immunized with either vaccine alone, vaccine plus 2 µg DHEA, vaccine plus 0.1 µg of 1,25(OH)$_2$D$_3$, or vaccine with both 2 µg DHEA and 0.1 μg 1,25(OH)$_2$D$_3$. The agents were incorporated directly into the vaccine mixture. Individual serum (systemic) samples and mucosal samples(vaginal lavages (75 μl of physiological saline)) were collected at weekly intervals during the primary response. FIGS. 14A–14D show the mean quantities of antibody detected in serum (A and B) and mucosal secretions (C and D) 21 days after a single immunization. The results show that co-administration of DHEA and 1,25(OH)$_2$D$_3$ in the vaccine synergistically enhances both the serum and mucosal antibody response.

Similar results are obtained for the DHEA congeners of Table A when substituted for DHEA.

EXAMPLE 19

Administration of DHEA and All Trans-Retinoic Acid in Vaccine Enhances Serum and Mucosal Antibody Response Groups of five mature adult CF1 mice were immunized with 1.0 μg rHBSAg in 25 μl of alum (273 μg/ml) in the hind footpad. The mice in each group were immunized with either vaccine alone, vaccine plus 5.0 μg of all trans-retinoic acid, or vaccine with both 2 μg DHEA and 5.0 μg all trans-retinoic acid. The agents were incorporated directly into the vaccine mixture. Individual serum (systemic) samples and mucosal samples (vaginal lavages (75 μl of physiological saline)) were collected at weekly intervals during the primary response. FIGS. 15A–15D show the mean quantities of antibody detected in serum (A and B) and mucosal secretions (C and D) 21 days after a single immunization. The results show that co-administration of DHEA and all trans-retinoic acid in the vaccine synergistically enhances both the serum and mucosal antibody response.

EXAMPLE 20

Figure 16A:
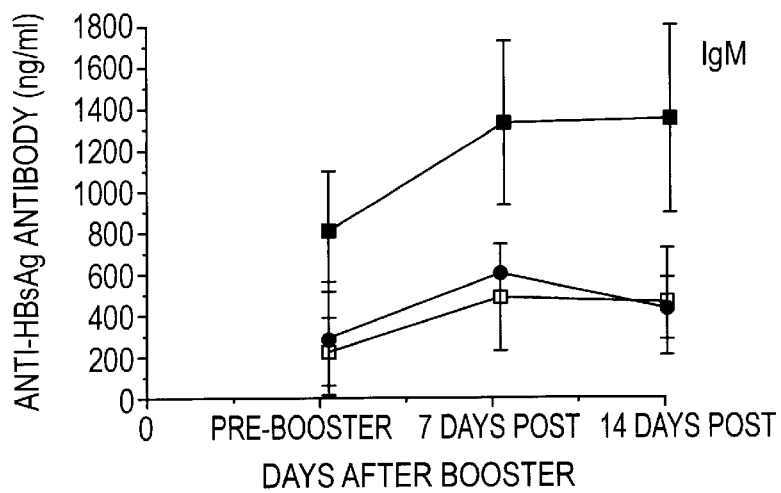
FIGS. 16A–16C show the specific serum IgM, IgG and IgA responses of neonatal mice to 1.0 $\mu$g rHBSAg. Responses are shown for two-week old mice treated with rHBSAg (□), two-week old mice treated with rHBSAg and 10 $\mu$g DHEA in the vaccine (●) and fully mature mice treated with rHBSAg (■).
Figure 16B:
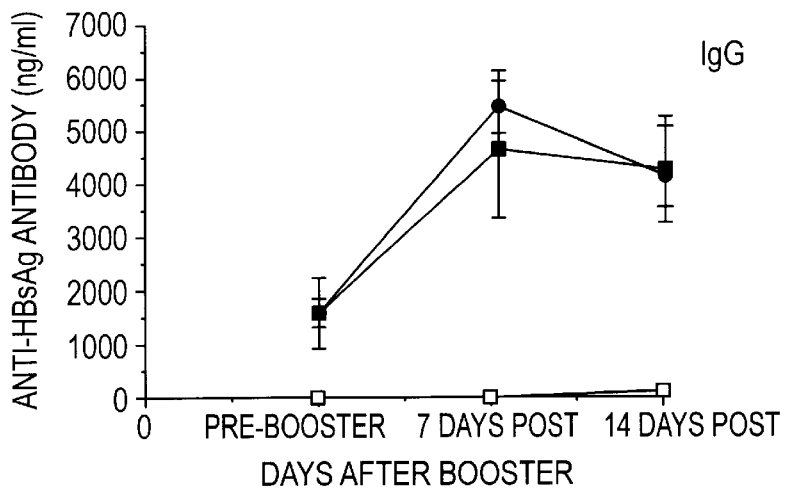
Figure 16C:
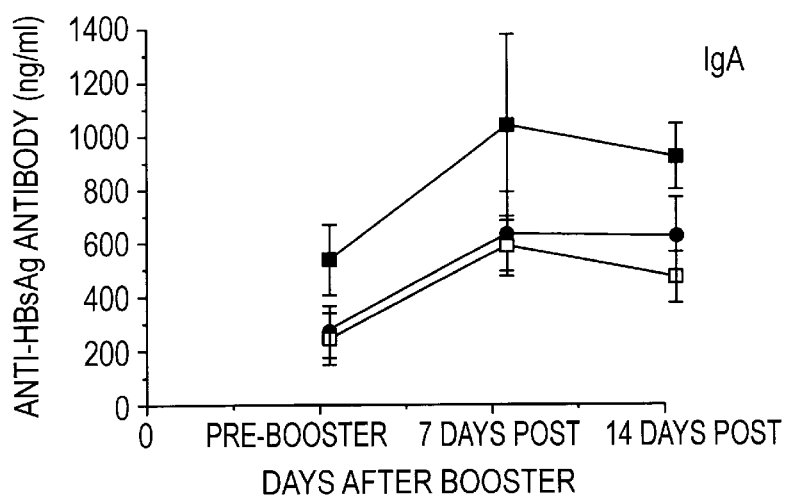

Administration of DHEA in a Vaccine Enhances Specific Immune Responses in Neonates Two-week old CF1 mice were immunized with 1.0 μg rHBSAg in 25 μl of alum (273 μg/ml). Another group of two-week old CF-1 mice were immunized identically, except that the composition included 10 μg DHEA. A third group of fully mature CF-1 mice were immunized with the 1.0 μg rHBSAg in alum by subcutaneously injection. After a six-week rest, individual serum samples were obtained and then all mice were re-immunized with 1.0 μg rHBSAg in alum by subcutaneous injection. No additional exposure to DHEA was supplied. Individual serum samples were again collected from all mice at one and two weeks past the booster immunization. The specific serum IgM, IgG and IgA response of neonatal mice to rHBSAg is shown in FIGS. 16A–16C. These figures show that the vaccination of neonatal mice with DHEA added to the rHBSAg vaccine influences the serum antibody response measured in these mice later on in life. A selective enhancement of IgG anti-rHBSAg antibody with no measurable enhancement of specific IgM and IgA antibody in young adult mice that received primary immunization during a pre-immunocompetent stage of life was observed.

EXAMPLE 21

Administration of 1,25(0H)$_{2-16}$-ene Vitamin D$_3$ in Vaccine Enhances Serum and Mucosal Antibody Response Groups of mature adult CF1 mice were immunized with 1.0 μg rHBSAg in 25 μl of alum (273 μg/ml) in the hind footpad. The mice in each group were immunized with either vaccine alone, vaccine plus 0.1 μg 1,25(OH)$_2$D$_3$, or 0.1 μg 1,25(OH)$_2$-16-ene D$_3$. The agents were incorporated directly into the vaccine mixture. Antibody production was followed over 30 days in individual serum samples, fecal samples and mucosal samples (vagninal lavages (75 μl of physiological saline)). Identical results were obtained with both 1,25(OH)$_2$D$_3$ and 1,25(OH)$_2$-16-ene D$_3$. These results were identical to those reported in the previous examples, i.e., an increase in both serum and mucosal IgG and IgA antibody levels when compared to the vaccine alone. In addition, increased IgA antibodies were seen in fecal samples for the vaccines containing 1,25(OH)$_2$D$_3$ and 1,25 (OH)$_2$-16-ene D$_3$, when compared to the vaccine alone.

The immunized mice were then challenged with 2.0 μg rHBSAg intranasally, and antibody production followed for 10 days. The antibody titres were measured in lung lavages (75 μl physiological saline) and in feces. The titre of anti-rHBSAg antibodies (IgG and IgA) was elevated for both the vaccines containing 1,25(OH)$_2$D$_3$ or 1,25(OH)$_2$-16-ene D$_3$ compared to vaccine alone. The titre of IgA in feces was also elevated but not as great as in the lung lavages.

EXAMPLE 22

Topical Administration of Calcipotriene Enhances Serum and Mucosal Antibody Response Groups of mature adult mice were immunized with 0.1 μg rHBSAg in 25 μl alum (273 μg/ml) in the hind footpad. One-third of the mice were treated with 0.5 μg 1,25(OH)$_2$D$_3$ by topical application at the site of immunization, 5 days after immunization. One-third of the mice were similarly treated with 0.5 μg calcipotriene. Antibody production was followed over 30 days in individual serum samples, fecal samples and mucosal samples (vaginal lavages (75 μl of physiological saline)). Identical results were obtained with 1,25(OH)$_2$D$_3$ as previously noted, i.e., increased production of serum and mucosal IgG and IgA antibodies in serum and mucosal secretions when compared to vaccine alone. In addition, increased production of IgA was seen in fecal samples when compared to vaccine alone.

Similar results as seen with 1,25(OH)$_2$D$_3$ were seen with calcipotriene except the serum IgG levels were not elevated as much as with 1,25(OH)$_2$D$_3$.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A vaccine composition comprising 1) an amount of a specific antigen, wherein said amount of specific antigen causes an immune response, and 2) an amount of a dehydroepiandrosterone (DHEA) congener in a physiologically acceptable carrier, wherein said congener is selected from the group consisting of i) a compound or ii) a pharmaceutically acceptable salt of said compound wherein said compound has the formula

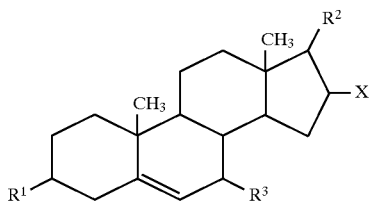

wherein

X is H or halogen;

R$^1$, R$^2$ and R$^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$; and R$^5$ and R$^6$ are independently —OH, pharmaceutically acceptable esters or pharmaceutically acceptable ethers; and wherein said amount of congener causes an increase of said immune response as compared to an immune response seen in the absence of said congener, with the proviso that said congener is not selected from the group consisting of 5-androstene-3β,17β-diol (AED) and 5-androstene-3β,17β,17β-triol (AET).

2. A vaccine composition comprising 1) an amount of a specific antigen, wherein said amount of specific antigen causes an immune response, and 2) an amount of a dehydroepiandrosterone (DHEA) congener in a physiologically acceptable carrier, wherein said DHEA congener is selected from the group consisting of DHEA, DHEAS and 16-α-bromo-DHEA.

3. The vaccine composition of claim 1 wherein the vaccine contains 0.1–1,000 μg of said congener.

4. The vaccine composition of claim 2 wherein the vaccine contains 0.1–1,000 μg of said congener.

5. The vaccine composition of claim 1 wherein said antigen is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

6. The vaccine composition of claim 2 wherein said antigen is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

7. A method for enhancing an antigen-specific cell-mediated immune response which comprises administering to an individual an amount of an immunomodulator as a vaccine adjuvant, wherein said amount of immunomodulator causes an enhanced antigen-specific cell-mediated immune response as compared to an antigen-specific cell-mediated immune response seen in the absence of said immunomodulator, said immunomodulator selected from the group consisting of 1) a dehydroepiandrosterone (DHEA) congener, wherein said DHEA congener is selected from the group consisting of i) a compound or ii) a pharmaceutically acceptable salt of said compound wherein said compound has the formula

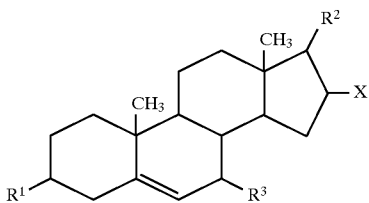

wherein

X is H or halogen;

R$^1$, R$^2$ and R$^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$; and R$^5$ and R$^6$ are independently —OH, pharmaceutically acceptable esters or pharmaceutically acceptable ethers and 2) a lymphoid organ modifying agent, wherein said lymphoid organ modifying agent is 1,25-dihydroxy Vitamin D$_3$, with the proviso that said convener is not selected from the group consisting of 5-androstene-3β, 17β-diol (AED) and 5-androstene-3β,7β,17β-triol (AET).

8. The method of claim 7 wherein the immunomodulator is administered up to three hours prior to vaccination.

9. The method of claim 7 wherein the immunomodulator is administered contemporaneously with vaccination.

10. The method of claim 7 wherein the immunomodulator is administered in a vaccine.

11. The method of claim 7 wherein said immunomodulator is said DHEA congener.

12. A method for enhancing an antigen-specific cell-mediated immune response which comprises administering to an individual an amount of an immunomodulator as a vaccine adjuvant, wherein said amount of immunomodulator causes an enhanced antigen-specific cell-mediated immune response as compared to an antigen-specific cell-mediated immune response seen in the absence of said immunomodulator, said immunomodulator selected from the group consisting of 1) a dehydroepiandrosterone (DHEA) congener wherein said DHEA congener is selected from the group consisting of DHEA, DHEAS and 16-α-bromo-DHEA and 2) a lymphoid organ modifying agent, wherein said lymphoid organ modifying agent is 1,25 dihydroxy vitamin D$_3$.

13. The method of claim 12 wherein said congener is DHEA.

14. The method of claim 12 wherein said congener is DHEAS.

15. The method of claim 12 wherein said compound is 16-α-bromo-DHEA.

16. The method of claim 12 wherein said immunomodulator is 1,25-dihydroxy Vitamin D$_3$.

17. The method of claim 12 wherein the amount of said DHEA congener is 0.1–1,000 μg.

18. The method of claim 7 wherein said immunomodulator is administered epicutaneously.

19. The method of claim 7 wherein said immunomodulator is administered intramuscularly.

20. The method of claim 7 wherein said immunomodulator is administered intradermally.

21. The method of claim 7 wherein the immunomodulator is administered subcutaneously.

22. The method of claim 7 wherein the immunomodulator is administered up to three hours after vaccination.

23. The method of claim 7 wherein the amount of said lymphoid organ modifying agent is 0.1–500 μg.

24. The method of claim 8 wherein said vaccination comprises an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

25. The method of claim 9 wherein said vaccination comprises an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

26. The method of claim 10 wherein said vaccine comprises an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

27. The method of claim 22 wherein said vaccination comprises an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

28. The method of claim 7 wherein said immunomodulator is administered topically.

29. A method for enhancing an antigen-specific CD4 T-cell function response which comprises administering to an individual an amount of an immunomodulator as a vaccine adjuvant, wherein said amount of immunomodulator causes an enhanced antigen-specific CD4 T-cell function response as compared to an antigen-specific CD4 T-cell function response seen in the absence of said immunomodulator, said immunomodulator selected from the group consisting of 1) a dehydroepiandrosterone (DHEA) congener, wherein said DHEA congener is selected from the group consisting of i) a compound or ii) a pharmaceutically acceptable salt of said compound wherein said compound has the formula

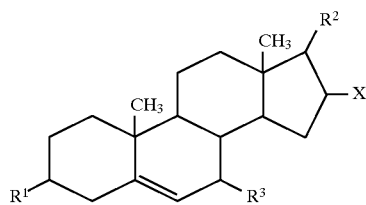

wherein
X is H or halogen;
R$^1$, R$^2$ and R$^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$; and
R$^5$ and R$^6$ are independently —OH, pharmaceutically acceptable esters or pharmaceutically acceptable ethers and 2) a lymphoid organ modifying agent, wherein said lymphoid organ modifying agent is 1,25-dihydroxy Vitamin D$_3$, with the proviso that said congener is not selected from the group consisting of 5-androstene-3β, 17β-diol (AED) and 5-androstene-3β,7β,17β-triol (AET).

30. The method of claim 29 wherein the immunomodulator is administered up to three hours prior to vaccination.

31. The method of claim 29 wherein the immunomodulator is administered contemporaneously with vaccination.

32. The method of claim 29 wherein the immunomodulator is administered in a vaccine.

33. The method of claim 29 wherein said immunomodulator is said DHEA congener.

34. A method for enhancing an antigen-specific CD4 T-cell function response which comprises administering to an individual an amount of an immunomodulator as a vaccine adjuvant, wherein said amount of immunomodulator causes an enhanced antigen-specific CD4 T-cell function response as compared to an antigen-specific CD4 T-cell function response seen in the absence of said immunomodulator, said immunomodulator selected from the group consisting of 1) a dehydroepiandrosterone (DHEA) congener, wherein said DHEA congener is selected from the group consisting of DHEA, DHEAS and 16-α-bromo-DHEA and 2) a lymphoid organ modifying agent, wherein said lymphoid organ modifying agent is 1,25-dihydroxy vitamin D$_3$.

35. The method of claim 34 wherein said congener is DHEA.

36. The method of claim 34 wherein said congener is DHEAS.

37. The method of claim 34 wherein said congener is 16-α-bromo-DHEA.

38. The method of claim 34 wherein said immunomodulator is 1,25-dihydroxy Vitamin D$_3$.

39. The method of claim 33 wherein the amount of said DHEA congener is 0.1–1,000 μg.

40. The method of claim 29 wherein said immunomodulator is administered epicutaneously.

41. The method of claim 29 wherein said immunomodulator is administered intramuscularly.

42. The method of claim 29 wherein said immunomodulator is administered intradermally.

43. The method of claim 29 wherein the immunomodulator is administered subcutaneously.

44. The method of claim 29 wherein the immunomodulator is administered up to three hours after vaccination.

45. The method of claim 38 wherein the amount of 1,25-dihydroxy Vitamin D$_3$ is 0.1–500 μg.

46. The method of claim 30 wherein said vaccination comprises an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

47. The method of claim 31 wherein said vaccination comprises an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

48. The method of claim 35 wherein said vaccine comprises an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

49. The method of claim 44 wherein said vaccination comprises an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

50. The method of claim 29 wherein said immunomodulator is administered topically.

* * * * *